United States Patent [19]
Mosley et al.

[11] Patent Number: 5,783,672
[45] Date of Patent: Jul. 21, 1998

[54] RECEPTOR FOR ONCOSTATIN M

[75] Inventors: Bruce Mosley, Seattle; David J. Cosman, Bainbridge Island, both of Wash.

[73] Assignee: Immunex Corporation, Seattle, Wash.

[21] Appl. No.: 308,881

[22] Filed: Sep. 12, 1994

Related U.S. Application Data

[63] Continuation-in-part of Ser. No. 249,553, May 26, 1994, abandoned.

[51] Int. Cl.$^6$ .................................................. C07K 14/715
[52] U.S. Cl. ......................... 530/350; 530/395; 530/402
[58] Field of Search ........................... 435/69.1; 530/350, 530/391.1, 391.9, 395

[56] References Cited

U.S. PATENT DOCUMENTS

| | | | |
|---|---|---|---|
| 5,073,627 | 12/1991 | Curtis et al. | 530/351 |
| 5,106,731 | 4/1992 | Salahuddin et al. | |
| 5,120,535 | 6/1992 | Marquardt et al. | 424/85.5 |
| 5,262,522 | 11/1993 | Gearing et al. | 530/350 |

FOREIGN PATENT DOCUMENTS

| | | |
|---|---|---|
| 0 290 948 | 11/1988 | European Pat. Off. |
| 0 411 946 A2 | 2/1991 | European Pat. Off. |
| 0 450 472 | 10/1991 | European Pat. Off. |
| WO 90/12585 | 11/1990 | WIPO |
| WO 91/09057 | 6/1991 | WIPO |
| WO 92/10570 | 6/1992 | WIPO |
| WO 92/21380 | 12/1992 | WIPO |
| WO 93/10151 | 5/1993 | WIPO |

OTHER PUBLICATIONS

Zarling et al., "Oncostatin M: A growth regulator produced by differentiated histiocytic lymphoma cells", *Proc. Natl. Acad. Sci. USA* 83:9739–9743, 1986.

Malik et al., "Molecular Cloning, Sequence Analysis, and Functional Expression of a Novel Growth Regulator, Oncostatin M", *Mol. Cell. Biol.* 9:2847–2953, 1989.

Linsley et al., "Identification and Characterization of Cellular Receptors for the Growth Regulator, Oncostatin M", *J. Biol. Chem.* 264:4282–4289, 1989.

Liu et al., "Interleukin–6 Signal Transducter gp130 Mediates Oncostatin M Signaling", *J. Biol. Chem.* 267:16763–16766, 1992.

Nair et al., "Identification of a Major Growth Factor for AIDS–Kaposi's Sarcoma Cells as Oncostatin M", *Science* 255:1430–1432, 1992.

Miles et al., "Oncostatin M as a Potent Mitogen for AIDS–Kaposi's Sarcoma–Derived Cells", *Science* 255:1432–1434, 1992.

Gearing et al., "The IL–6 Signal Transducer, gp130: An Oncostatin M Receptor and Affinity Converter for the LIF receptor", *Science* 255:1434–1437, 1992.

Gearing and Bruce, "Oncostatin M Binds the High–Affinity Leukemia Inhibitory Factor Receptor", *The New Biologist* 4:61–65, 1992.

Hibi et al., "Molecular Cloning and Expression of an IL–6 Signal Transducer, gp130", *Cell* 63:1149–1157, 1990.

Gearing et al., "Leukemia inhibitory factor receptor is structurally related to the IL–6 signal transducer, gp130", *EMBO J.* 10:2839–2848, 1991.

Brown et al., "Regulation of IL–6 Expression by Oncostatin M", *J. Immunol.* 147:2175–2180, 1991.

De Wit et al., "Interleukin–6 concentrations in the serum of patients with AIDS–associated Kaposi's sarcoma during treatment with interferon–alpha", *J. Int. Med.* 229:539–542, 1991.

Gearing et al., "Reconstitution of high affinity leukemia inhibitory factor (LIF) receptors in haemopoietic cells transfected with the cloned human LIF receptor", Ciba Foundation Symposium 167:245–255, 1992.

Thoma et al., "Discrimination Between Two Types of Receptors for Oncostatin M: Signal Transduction via MAP Kinase", Keystone Symposia, Keystone, CO, Jan. 31–Feb. 7, 1993.

Thoma et al., "Oncostatin M and Leukemia Inhibitory Factor Trigger Overlapping and Different Signals Through Partially Shared Receptor Complexes", *J. Biol. Chem.* 269:6215–6222, 1994.

Gearing et al., "Proliferative responses and binding properties of hematopoietic cells transfected with low–affinity receptors for leukemia inhibitory factor, oncostatin M, and ciliary neurotrophic factor", *Proc. Natl. Acad. Sci. USA* 91:1119–1123, 1994.

Ashkenazi et al., "Protection against endotoxic shock by a tumor necrosis factor receptor immunoadhesin", *Proc. Natl. Acad. Sci. USA* 88:10535–10539, 1991.

Byrn et al., "Biological properties of a CD4 immunoadhesin", *Nature* 344:667–670, 1990.

Baumann et al., "Reconstitution of the Response to Leukemia Inhibitory Factor, Oncostatin M, and Ciliary Neurotrophic Factor in Hepatoma Cells", *J. Biol. Chem.* 268:8414–8417, 1993.

Cai et al., "Oncostatin M Is an Autocrine Growth Factor in Kaposi's Sarcoma", *Amer. J. Path.* 145:74–79, 1994.

Takeshita et al., "Cloning of the γ Chain of the Human IL–2 receptor", *Science* 257:379–382, 1992.

Park et al., "The LIF/Oncostatin M Receptor System: A Multi–Subunit Cytokine Receptor Family", Abstract and presentation at workshop on Intra–and Extra–Cellular Signalling in Hematopoiesis, Madrid, May 25–27, 1993.

Liu et al., "Interactions Between Oncostatin M and the IL–6 Signal Transducer, gp130," *Cytokine* 6 (3):272–278, May 1994.

*Primary Examiner*—Paula K. Hutzell
*Assistant Examiner*—Stephen Gucker
*Attorney, Agent, or Firm*—Kathryn A. Anderson

[57] ABSTRACT

A novel polypeptide functions as the β chain of an oncostatin M receptor and is thus designated OSM-Rβ. Heterodimeric receptor proteins comprising OSM-Rβ and gp130 bind oncostatin M and find use in inhibiting biological activities mediated by oncostatin M.

13 Claims, 3 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2369 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( v i ) ORIGINAL SOURCE:
        ( F ) TISSUE TYPE: human placenta ( v i i ) IMMEDIATE SOURCE:
        ( B ) CLONE: B10G/pDC303

( i x ) FEATURE:
        ( A ) NAME/KEY: CDS
        ( B ) LOCATION: 244..2369

( i x ) FEATURE:
        ( A ) NAME/KEY: mat_peptide
        ( B ) LOCATION: 310..2369

( i x ) FEATURE:
        ( A ) NAME/KEY: sig_peptide
        ( B ) LOCATION: 244..309

( x i ) SEQUENCE DESCRIPTION: SEQ ID NO:1:

```
GGCCCGCGGA  GTCGCGCTGG  GCCGCCCCGG  CGCAGCTGAA  CCGGGGGCCG  CGCCTGCCAG      60

GCCGACGGGT  CTGGCCCAGC  CTGGCGCCAA  GGGGTTCGTG  CGCTGTGGAG  ACGCGGAGGG     120

TCGAGGCGGC  GCGGCCTGAG  TGAAACCCAA  TGGAAAAAGC  ATGACATTTA  GAAGTAGAAG     180

ACTTAGCTTC  AAATCCCTAC  TCCTTCACTT  ACTAATTTTG  TGATTTGGAA  ATATCCGCGC     240

AAG ATG TTG ACG TTG CAG ACT TGG CTA GTG CAA GCC TTG TTT ATT TTC            288
    Met Leu Thr Leu Gln Thr Trp Leu Val Gln Ala Leu Phe Ile Phe
    -22     -20             -15                 -10

CTC ACC ACT GAA TCT ACA GGT GAA CTT CTA GAT CCA TGT GGT TAT ATC            336
Leu Thr Thr Glu Ser Thr Gly Glu Leu Leu Asp Pro Cys Gly Tyr Ile
            -5                  1                   5

AGT CCT GAA TCT CCA GTT GTA CAA CTT CAT TCT AAT TTC ACT GCA GTT            384
Ser Pro Glu Ser Pro Val Val Gln Leu His Ser Asn Phe Thr Ala Val
```

|  |  |  |  |  |  |  |  |  |  |  |  |  |  |  |  |  |
|---|---|---|---|---|---|---|---|---|---|---|---|---|---|---|---|---|
| | | 10 | | | | 15 | | | | 20 | | | | 25 | | |
| TGT | GTG | CTA | AAG | GAA | AAA | TGT | ATG | GAT | TAT | TTT | CAT | GTA | AAT | GCT | AAT | 432 |
| Cys | Val | Leu | Lys | Glu 30 | Lys | Cys | Met | Asp | Tyr 35 | Phe | His | Val | Asn | Ala 40 | Asn | |
| TAC | ATT | GTC | TGG | AAA | ACA | AAC | CAT | TTT | ACT | ATT | CCT | AAG | GAG | CAA | TAT | 480 |
| Tyr | Ile | Val | Trp 45 | Lys | Thr | Asn | His | Phe 50 | Thr | Ile | Pro | Lys | Glu 55 | Gln | Tyr | |
| ACT | ATC | ATA | AAC | AGA | ACA | GCA | TCC | AGT | GTC | ACC | TTT | ACA | GAT | ATA | GCT | 528 |
| Thr | Ile | Ile | Asn 60 | Arg | Thr | Ala | Ser 65 | Ser | Val | Thr | Phe | Thr 70 | Asp | Ile | Ala | |
| TCA | TTA | AAT | ATT | CAG | CTC | ACT | TGC | AAC | ATT | CTT | ACA | TTC | GGA | CAG | CTT | 576 |
| Ser | Leu 75 | Asn | Ile | Gln | Leu | Thr 80 | Cys | Asn | Ile | Leu | Thr 85 | Phe | Gly | Gln | Leu | |
| GAA | CAG | AAT | GTT | TAT | GGA | ATC | ACA | ATA | ATT | TCA | GGC | TTG | CCT | CCA | GAA | 624 |
| Glu 90 | Gln | Asn | Val | Tyr | Gly 95 | Ile | Thr | Ile | Ile | Ser 100 | Gly | Leu | Pro | Pro | Glu 105 | |
| AAA | CCT | AAA | AAT | TTG | AGT | TGC | ATT | GTG | AAC | GAG | GGG | AAG | AAA | ATG | AGG | 672 |
| Lys | Pro | Lys | Asn | Leu 110 | Ser | Cys | Ile | Val | Asn 115 | Glu | Gly | Lys | Lys | Met 120 | Arg | |
| TGT | GAG | TGG | GAT | GGT | GGA | AGG | GAA | ACA | CAC | TTG | GAG | ACA | AAC | TTC | ACT | 720 |
| Cys | Glu | Trp | Asp 125 | Gly | Gly | Arg | Glu | Thr 130 | His | Leu | Glu | Thr | Asn 135 | Phe | Thr | |
| TTA | AAA | TCT | GAA | TGG | GCA | ACA | CAC | AAG | TTT | GCT | GAT | TGC | AAA | GCA | AAA | 768 |
| Leu | Lys | Ser 140 | Glu | Trp | Ala | Thr | His 145 | Lys | Phe | Ala | Asp | Cys 150 | Lys | Ala | Lys | |
| CGT | GAC | ACC | CCC | ACC | TCA | TGC | ACT | GTT | GAT | TAT | TCT | ACT | GTG | TAT | TTT | 816 |
| Arg | Asp 155 | Thr | Pro | Thr | Ser | Cys 160 | Thr | Val | Asp | Tyr | Ser 165 | Thr | Val | Tyr | Phe | |
| GTC | AAC | ATT | GAA | GTC | TGG | GTA | GAA | GCA | GAG | AAT | GCC | CTT | GGG | AAG | GTT | 864 |
| Val 170 | Asn | Ile | Glu | Val | Trp 175 | Val | Glu | Ala | Glu | Asn 180 | Ala | Leu | Gly | Lys | Val 185 | |
| ACA | TCA | GAT | CAT | ATC | AAT | TTT | GAT | CCT | GTA | TAT | AAA | GTG | AAG | CCC | AAT | 912 |
| Thr | Ser | Asp | His | Ile 190 | Asn | Phe | Asp | Pro | Val 195 | Tyr | Lys | Val | Lys | Pro 200 | Asn | |
| CCG | CCA | CAT | AAT | TTA | TCA | GTG | ATC | AAC | TCA | GAG | GAA | CTG | TCT | AGT | ATC | 960 |
| Pro | Pro | His | Asn 205 | Leu | Ser | Val | Ile | Asn 210 | Ser | Glu | Glu | Leu | Ser 215 | Ser | Ile | |
| TTA | AAA | TTG | ACA | TGG | ACC | AAC | CCA | AGT | ATT | AAG | AGT | GTT | ATA | ATA | CTA | 1008 |
| Leu | Lys | Leu 220 | Thr | Trp | Thr | Asn | Pro 225 | Ser | Ile | Lys | Ser | Val 230 | Ile | Ile | Leu | |
| AAA | TAT | AAC | ATT | CAA | TAT | AGG | ACC | AAA | GAT | GCC | TCA | ACT | TGG | AGC | CAG | 1056 |
| Lys | Tyr | Asn 235 | Ile | Gln | Tyr | Arg | Thr 240 | Lys | Asp | Ala | Ser | Thr 245 | Trp | Ser | Gln | |
| ATT | CCT | CCT | GAA | GAC | ACA | GCA | TCC | ACC | CGA | TCT | TCA | TTC | ACT | GTC | CAA | 1104 |
| Ile 250 | Pro | Pro | Glu | Asp | Thr 255 | Ala | Ser | Thr | Arg | Ser 260 | Ser | Phe | Thr | Val | Gln 265 | |
| GAC | CTT | AAA | CCT | TTT | ACA | GAA | TAT | GTG | TTT | AGG | ATT | CGC | TGT | ATG | AAG | 1152 |
| Asp | Leu | Lys | Pro | Phe 270 | Thr | Glu | Tyr | Val | Phe 275 | Arg | Ile | Arg | Cys | Met 280 | Lys | |
| GAA | GAT | GGT | AAG | GGA | TAC | TGG | AGT | GAC | TGG | AGT | GAA | GAA | GCA | AGT | GGG | 1200 |
| Glu | Asp | Gly | Lys 285 | Gly | Tyr | Trp | Ser | Asp 290 | Trp | Ser | Glu | Glu | Ala 295 | Ser | Gly | |
| ATC | ACC | TAT | GAA | GAT | AGA | CCA | TCT | AAA | GCA | CCA | AGT | TTC | TGG | TAT | AAA | 1248 |
| Ile | Thr | Tyr 300 | Glu | Asp | Arg | Pro | Ser 305 | Lys | Ala | Pro | Ser | Phe 310 | Trp | Tyr | Lys | |
| ATA | GAT | CCA | TCC | CAT | ACT | CAA | GGC | TAC | AGA | ACT | GTA | CAA | CTC | GTG | TGG | 1296 |
| Ile | Asp | Pro | Ser 315 | His | Thr | Gln | Gly | Tyr 320 | Arg | Thr | Val | Gln | Leu 325 | Val | Trp | |
| AAG | ACA | TTG | CCT | CCT | TTT | GAA | GCC | AAT | GGA | AAA | ATC | TTG | GAT | TAT | GAA | 1344 |
| Lys | Thr | Leu | Pro | Pro | Phe | Glu | Ala | Asn | Gly | Lys | Ile | Leu | Asp | Tyr | Glu | |

-continued

| | | | | | | | | | | | | | | | | |
|---|---|---|---|---|---|---|---|---|---|---|---|---|---|---|---|---|
| 330 | | | | | 335 | | | | | 340 | | | | | 345 | |

| GTG | ACT | CTC | ACA | AGA | TGG | AAA | TCA | CAT | TTA | CAA | AAT | TAC | ACA | GTT | AAT | 1392 |
|---|---|---|---|---|---|---|---|---|---|---|---|---|---|---|---|---|
| Val | Thr | Leu | Thr | Arg | Trp | Lys | Ser | His | Leu | Gln | Asn | Tyr | Thr | Val | Asn | |
| | | | | 350 | | | | | 355 | | | | | 360 | | |

| GCC | ACA | AAA | CTG | ACA | GTA | AAT | CTC | ACA | AAT | GAT | CGC | TAT | CTA | GCA | ACC | 1440 |
|---|---|---|---|---|---|---|---|---|---|---|---|---|---|---|---|---|
| Ala | Thr | Lys | Leu | Thr | Val | Asn | Leu | Thr | Asn | Asp | Arg | Tyr | Leu | Ala | Thr | |
| | | | 365 | | | | | 370 | | | | | 375 | | | |

| CTA | ACA | GTA | AGA | AAT | CTT | GTT | GGC | AAA | TCA | GAT | GCA | GCT | GTT | TTA | ACT | 1488 |
|---|---|---|---|---|---|---|---|---|---|---|---|---|---|---|---|---|
| Leu | Thr | Val | Arg | Asn | Leu | Val | Gly | Lys | Ser | Asp | Ala | Ala | Val | Leu | Thr | |
| | | | 380 | | | | | 385 | | | | | 390 | | | |

| ATC | CCT | GCC | TGT | GAC | TTT | CAA | GCT | ACT | CAC | CCT | GTA | ATG | GAT | CTT | AAA | 1536 |
|---|---|---|---|---|---|---|---|---|---|---|---|---|---|---|---|---|
| Ile | Pro | Ala | Cys | Asp | Phe | Gln | Ala | Thr | His | Pro | Val | Met | Asp | Leu | Lys | |
| | | 395 | | | | | 400 | | | | | 405 | | | | |

| GCA | TTC | CCC | AAA | GAT | AAC | ATG | CTT | TGG | GTG | GAA | TGG | ACT | ACT | CCA | AGG | 1584 |
|---|---|---|---|---|---|---|---|---|---|---|---|---|---|---|---|---|
| Ala | Phe | Pro | Lys | Asp | Asn | Met | Leu | Trp | Val | Glu | Trp | Thr | Thr | Pro | Arg | |
| 410 | | | | | 415 | | | | | 420 | | | | | 425 | |

| GAA | TCT | GTA | AAG | AAA | TAT | ATA | CTT | GAG | TGG | TGT | GTG | TTA | TCA | GAT | AAA | 1632 |
|---|---|---|---|---|---|---|---|---|---|---|---|---|---|---|---|---|
| Glu | Ser | Val | Lys | Lys | Tyr | Ile | Leu | Glu | Trp | Cys | Val | Leu | Ser | Asp | Lys | |
| | | | | 430 | | | | | 435 | | | | | 440 | | |

| GCA | CCC | TGT | ATC | ACA | GAC | TGG | CAA | CAA | GAA | GAT | GGT | ACC | GTG | CAT | CGC | 1680 |
|---|---|---|---|---|---|---|---|---|---|---|---|---|---|---|---|---|
| Ala | Pro | Cys | Ile | Thr | Asp | Trp | Gln | Gln | Glu | Asp | Gly | Thr | Val | His | Arg | |
| | | | 445 | | | | | 450 | | | | | 455 | | | |

| ACC | TAT | TTA | AGA | GGG | AAC | TTA | GCA | GAG | AGC | AAA | TGC | TAT | TTG | ATA | ACA | 1728 |
|---|---|---|---|---|---|---|---|---|---|---|---|---|---|---|---|---|
| Thr | Tyr | Leu | Arg | Gly | Asn | Leu | Ala | Glu | Ser | Lys | Cys | Tyr | Leu | Ile | Thr | |
| | | | 460 | | | | | 465 | | | | | 470 | | | |

| GTT | ACT | CCA | GTA | TAT | GCT | GAT | GGA | CCA | GGA | AGC | CCT | GAA | TCC | ATA | AAG | 1776 |
|---|---|---|---|---|---|---|---|---|---|---|---|---|---|---|---|---|
| Val | Thr | Pro | Val | Tyr | Ala | Asp | Gly | Pro | Gly | Ser | Pro | Glu | Ser | Ile | Lys | |
| | | 475 | | | | | 480 | | | | | 485 | | | | |

| GCA | TAC | CTT | AAA | CAA | GCT | CCA | CCT | TCC | AAA | GGA | CCT | ACT | GTT | CGG | ACA | 1824 |
|---|---|---|---|---|---|---|---|---|---|---|---|---|---|---|---|---|
| Ala | Tyr | Leu | Lys | Gln | Ala | Pro | Pro | Ser | Lys | Gly | Pro | Thr | Val | Arg | Thr | |
| 490 | | | | | 495 | | | | | 500 | | | | | 505 | |

| AAA | AAA | GTA | GGG | AAA | AAC | GAA | GCT | GTC | TTA | GAG | TGG | GAC | CAA | CTT | CCT | 1872 |
|---|---|---|---|---|---|---|---|---|---|---|---|---|---|---|---|---|
| Lys | Lys | Val | Gly | Lys | Asn | Glu | Ala | Val | Leu | Glu | Trp | Asp | Gln | Leu | Pro | |
| | | | | 510 | | | | | 515 | | | | | 520 | | |

| GTT | GAT | GTT | CAG | AAT | GGA | TTT | ATC | AGA | AAT | TAT | ACT | ATA | TTT | TAT | AGA | 1920 |
|---|---|---|---|---|---|---|---|---|---|---|---|---|---|---|---|---|
| Val | Asp | Val | Gln | Asn | Gly | Phe | Ile | Arg | Asn | Tyr | Thr | Ile | Phe | Tyr | Arg | |
| | | | 525 | | | | | 530 | | | | | 535 | | | |

| ACC | ATC | ATT | GGA | AAT | GAA | ACT | GCT | GTG | AAT | GTG | GAT | TCT | TCC | CAC | ACA | 1968 |
|---|---|---|---|---|---|---|---|---|---|---|---|---|---|---|---|---|
| Thr | Ile | Ile | Gly | Asn | Glu | Thr | Ala | Val | Asn | Val | Asp | Ser | Ser | His | Thr | |
| | | | 540 | | | | | 545 | | | | | 550 | | | |

| GAA | TAT | ACA | TTG | TCC | TCT | TTG | ACT | AGT | GAC | ACA | TTG | TAC | ATG | GTA | CGA | 2016 |
|---|---|---|---|---|---|---|---|---|---|---|---|---|---|---|---|---|
| Glu | Tyr | Thr | Leu | Ser | Ser | Leu | Thr | Ser | Asp | Thr | Leu | Tyr | Met | Val | Arg | |
| | | 555 | | | | | 560 | | | | | 565 | | | | |

| ATG | GCA | GCA | TAC | ACA | GAT | GAA | GGT | GGG | AAG | GAT | GGT | CCA | GAA | TTC | ACT | 2064 |
|---|---|---|---|---|---|---|---|---|---|---|---|---|---|---|---|---|
| Met | Ala | Ala | Tyr | Thr | Asp | Glu | Gly | Gly | Lys | Asp | Gly | Pro | Glu | Phe | Thr | |
| 570 | | | | | 575 | | | | | 580 | | | | | 585 | |

| TTT | ACT | ACC | CCA | AAG | TTT | GCT | CAA | GGA | GAA | ATT | GAA | GCC | ATA | GTC | GTG | 2112 |
|---|---|---|---|---|---|---|---|---|---|---|---|---|---|---|---|---|
| Phe | Thr | Thr | Pro | Lys | Phe | Ala | Gln | Gly | Glu | Ile | Glu | Ala | Ile | Val | Val | |
| | | | | 590 | | | | | 595 | | | | | 600 | | |

| CCT | GTT | TGC | TTA | GCA | TTC | CTA | TTG | ACA | ACT | CTT | CTG | GGA | GTG | CTG | TTC | 2160 |
|---|---|---|---|---|---|---|---|---|---|---|---|---|---|---|---|---|
| Pro | Val | Cys | Leu | Ala | Phe | Leu | Leu | Thr | Thr | Leu | Leu | Gly | Val | Leu | Phe | |
| | | | 605 | | | | | 610 | | | | | 615 | | | |

| TGC | TTT | AAT | AAG | CGA | GAC | CTA | ATT | AAA | AAA | CAC | ATC | TGG | CCT | AAT | GTT | 2208 |
|---|---|---|---|---|---|---|---|---|---|---|---|---|---|---|---|---|
| Cys | Phe | Asn | Lys | Arg | Asp | Leu | Ile | Lys | Lys | His | Ile | Trp | Pro | Asn | Val | |
| | | | 620 | | | | | 625 | | | | | 630 | | | |

| CCA | GAT | CCT | TCA | AAG | AGT | CAT | ATT | GCC | CAG | TGG | TCA | CCT | CAC | ACT | CCT | 2256 |
|---|---|---|---|---|---|---|---|---|---|---|---|---|---|---|---|---|
| Pro | Asp | Pro | Ser | Lys | Ser | His | Ile | Ala | Gln | Trp | Ser | Pro | His | Thr | Pro | |
| | | | 635 | | | | | 640 | | | | | 645 | | | |

| CCA | AGG | CAC | AAT | TTT | AAT | TCA | AAA | GAT | CAA | ATG | TAT | TCA | GAT | GGC | AAT | 2304 |
|---|---|---|---|---|---|---|---|---|---|---|---|---|---|---|---|---|
| Pro | Arg | His | Asn | Phe | Asn | Ser | Lys | Asp | Gln | Met | Tyr | Ser | Asp | Gly | Asn | |

```
650                        655                        660                        665
TTC  ACT  GAT  GTA  AGT  GTT  GTG  GAA  ATA  GAA  GCA  AAT  GAC  AAA  AAG  CCT       2352
Phe  Thr  Asp  Val  Ser  Val  Val  Glu  Ile  Glu  Ala  Asn  Asp  Lys  Lys  Pro
                    670                       675                       680

TTT  CCA  GAA  GAT  CTG  AA                                                          2369
Phe  Pro  Glu  Asp  Leu
               685
```

( 2 ) INFORMATION FOR SEQ ID NO:2:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Thr  Leu  Gln  Thr  Trp  Leu  Val  Gln  Ala  Leu  Phe  Ile  Phe  Leu
-22       -20                      -15                      -10

Thr  Thr  Glu  Ser  Thr  Gly  Glu  Leu  Leu  Asp  Pro  Cys  Gly  Tyr  Ile  Ser
     -5                       1                  5                            10

Pro  Glu  Ser  Pro  Val  Val  Gln  Leu  His  Ser  Asn  Phe  Thr  Ala  Val  Cys
                    15                  20                       25

Val  Leu  Lys  Glu  Lys  Cys  Met  Asp  Tyr  Phe  His  Val  Asn  Ala  Asn  Tyr
               30                  35                            40

Ile  Val  Trp  Lys  Thr  Asn  His  Phe  Thr  Ile  Pro  Lys  Glu  Gln  Tyr  Thr
               45                  50                       55

Ile  Ile  Asn  Arg  Thr  Ala  Ser  Ser  Val  Thr  Phe  Thr  Asp  Ile  Ala  Ser
          60                  65                       70

Leu  Asn  Ile  Gln  Leu  Thr  Cys  Asn  Ile  Leu  Thr  Phe  Gly  Gln  Leu  Glu
75                       80                  85                            90

Gln  Asn  Val  Tyr  Gly  Ile  Thr  Ile  Ile  Ser  Gly  Leu  Pro  Pro  Glu  Lys
                    95                  100                      105

Pro  Lys  Asn  Leu  Ser  Cys  Ile  Val  Asn  Glu  Gly  Lys  Lys  Met  Arg  Cys
               110                 115                      120

Glu  Trp  Asp  Gly  Gly  Arg  Glu  Thr  His  Leu  Glu  Thr  Asn  Phe  Thr  Leu
          125                 130                      135

Lys  Ser  Glu  Trp  Ala  Thr  His  Lys  Phe  Ala  Asp  Cys  Lys  Ala  Lys  Arg
     140                 145                      150

Asp  Thr  Pro  Thr  Ser  Cys  Thr  Val  Asp  Tyr  Ser  Thr  Val  Tyr  Phe  Val
155                 160                      165                           170

Asn  Ile  Glu  Val  Trp  Val  Glu  Ala  Glu  Asn  Ala  Leu  Gly  Lys  Val  Thr
                    175                 180                      185

Ser  Asp  His  Ile  Asn  Phe  Asp  Pro  Val  Tyr  Lys  Val  Lys  Pro  Asn  Pro
               190                 195                      200

Pro  His  Asn  Leu  Ser  Val  Ile  Asn  Ser  Glu  Glu  Leu  Ser  Ser  Ile  Leu
          205                 210                      215

Lys  Leu  Thr  Trp  Thr  Asn  Pro  Ser  Ile  Lys  Ser  Val  Ile  Ile  Leu  Lys
     220                 225                      230

Tyr  Asn  Ile  Gln  Tyr  Arg  Thr  Lys  Asp  Ala  Ser  Thr  Trp  Ser  Gln  Ile
235                 240                      245                           250

Pro  Pro  Glu  Asp  Thr  Ala  Ser  Thr  Arg  Ser  Ser  Phe  Thr  Val  Gln  Asp
               255                 260                      265

Leu  Lys  Pro  Phe  Thr  Glu  Tyr  Val  Phe  Arg  Ile  Arg  Cys  Met  Lys  Glu
          270                 275                      280

Asp  Gly  Lys  Gly  Tyr  Trp  Ser  Asp  Trp  Ser  Glu  Glu  Ala  Ser  Gly  Ile
```

-continued

|   |   |   |   |   | 285 |   |   |   |   | 290 |   |   |   |   | 295 |   |   |
|---|---|---|---|---|---|---|---|---|---|---|---|---|---|---|---|---|---|

Thr Tyr Glu Asp Arg Pro Ser Lys Ala Pro Ser Phe Trp Tyr Lys Ile
300                          305                310

Asp Pro Ser His Thr Gln Gly Tyr Arg Thr Val Gln Leu Val Trp Lys
315                    320                325                    330

Thr Leu Pro Pro Phe Glu Ala Asn Gly Lys Ile Leu Asp Tyr Glu Val
              335                    340                345

Thr Leu Thr Arg Trp Lys Ser His Leu Gln Asn Tyr Thr Val Asn Ala
           350                    355                360

Thr Lys Leu Thr Val Asn Leu Thr Asn Asp Arg Tyr Leu Ala Thr Leu
         365                    370                375

Thr Val Arg Asn Leu Val Gly Lys Ser Asp Ala Ala Val Leu Thr Ile
      380                    385                390

Pro Ala Cys Asp Phe Gln Ala Thr His Pro Val Met Asp Leu Lys Ala
395                    400                405                    410

Phe Pro Lys Asp Asn Met Leu Trp Val Glu Trp Thr Thr Pro Arg Glu
              415                    420                425

Ser Val Lys Lys Tyr Ile Leu Glu Trp Cys Val Leu Ser Asp Lys Ala
           430                    435                440

Pro Cys Ile Thr Asp Trp Gln Gln Glu Asp Gly Thr Val His Arg Thr
         445                    450                455

Tyr Leu Arg Gly Asn Leu Ala Glu Ser Lys Cys Tyr Leu Ile Thr Val
      460                    465                470

Thr Pro Val Tyr Ala Asp Gly Pro Gly Ser Pro Glu Ser Ile Lys Ala
475                    480                485                    490

Tyr Leu Lys Gln Ala Pro Pro Ser Lys Gly Pro Thr Val Arg Thr Lys
              495                    500                505

Lys Val Gly Lys Asn Glu Ala Val Leu Glu Trp Asp Gln Leu Pro Val
           510                    515                520

Asp Val Gln Asn Gly Phe Ile Arg Asn Tyr Thr Ile Phe Tyr Arg Thr
         525                    530                535

Ile Ile Gly Asn Glu Thr Ala Val Asn Val Asp Ser Ser His Thr Glu
      540                    545                550

Tyr Thr Leu Ser Ser Leu Thr Ser Asp Thr Leu Tyr Met Val Arg Met
555                    560                565                    570

Ala Ala Tyr Thr Asp Glu Gly Gly Lys Asp Gly Pro Glu Phe Thr Phe
              575                    580                585

Thr Thr Pro Lys Phe Ala Gln Gly Glu Ile Glu Ala Ile Val Val Pro
           590                    595                600

Val Cys Leu Ala Phe Leu Leu Thr Thr Leu Leu Gly Val Leu Phe Cys
         605                    610                615

Phe Asn Lys Arg Asp Leu Ile Lys Lys His Ile Trp Pro Asn Val Pro
      620                    625                630

Asp Pro Ser Lys Ser His Ile Ala Gln Trp Ser Pro His Thr Pro Pro
635                    640                645                    650

Arg His Asn Phe Asn Ser Lys Asp Gln Met Tyr Ser Asp Gly Asn Phe
              655                    660                665

Thr Asp Val Ser Val Val Glu Ile Glu Ala Asn Asp Lys Lys Pro Phe
           670                    675                680

Pro Glu Asp Leu
         685

( 2 ) INFORMATION FOR SEQ ID NO:3:

( i ) SEQUENCE CHARACTERISTICS:
    ( A ) LENGTH: 705 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
    ( B ) CLONE: hIgG1Fc ( i x ) FEATURE:
    ( A ) NAME/KEY: CDS
    ( B ) LOCATION: 1..699

( x i ) SEQUENCE DESCRIPTION: SEQ ID NO:3:

```
GAG  CCC  AGA  TCT  TGT  GAC  AAA  ACT  CAC  ACA  TGC  CCA  CCG  TGC  CCA  GCA      48
Glu  Pro  Arg  Ser  Cys  Asp  Lys  Thr  His  Thr  Cys  Pro  Pro  Cys  Pro  Ala
  1              5                       10                      15

CCT  GAA  CTC  CTG  GGG  GGA  CCG  TCA  GTC  TTC  CTC  TTC  CCC  CCA  AAA  CCC      96
Pro  Glu  Leu  Leu  Gly  Gly  Pro  Ser  Val  Phe  Leu  Phe  Pro  Pro  Lys  Pro
                      20                      25                      30

AAG  GAC  ACC  CTC  ATG  ATC  TCC  CGG  ACC  CCT  GAG  GTC  ACA  TGC  GTG  GTG     144
Lys  Asp  Thr  Leu  Met  Ile  Ser  Arg  Thr  Pro  Glu  Val  Thr  Cys  Val  Val
             35                      40                      45

GTG  GAC  GTG  AGC  CAC  GAA  GAC  CCT  GAG  GTC  AAG  TTC  AAC  TGG  TAC  GTG     192
Val  Asp  Val  Ser  His  Glu  Asp  Pro  Glu  Val  Lys  Phe  Asn  Trp  Tyr  Val
        50                      55                      60

GAC  GGC  GTG  GAG  GTG  CAT  AAT  GCC  AAG  ACA  AAG  CCG  CGG  GAG  GAG  CAG     240
Asp  Gly  Val  Glu  Val  His  Asn  Ala  Lys  Thr  Lys  Pro  Arg  Glu  Glu  Gln
Asp  65                      70                      75                      80

TAC  AAC  AGC  ACG  TAC  CGG  GTG  GTC  AGC  GTC  CTC  ACC  GTC  CTG  CAC  CAG     288
Tyr  Asn  Ser  Thr  Tyr  Arg  Val  Val  Ser  Val  Leu  Thr  Val  Leu  His  Gln
                      85                      90                      95

GAC  TGG  CTG  AAT  GGC  AAG  GAC  TAC  AAG  TGC  AAG  GTC  TCC  AAC  AAA  GCC     336
Asp  Trp  Leu  Asn  Gly  Lys  Asp  Tyr  Lys  Cys  Lys  Val  Ser  Asn  Lys  Ala
             100                     105                     110

CTC  CCA  GCC  CCC  ATG  CAG  AAA  ACC  ATC  TCC  AAA  GCC  AAA  GGG  CAG  CCC     384
Leu  Pro  Ala  Pro  Met  Gln  Lys  Thr  Ile  Ser  Lys  Ala  Lys  Gly  Gln  Pro
        115                     120                     125

CGA  GAA  CCA  CAG  GTG  TAC  ACC  CTG  CCC  CCA  TCC  CGG  GAT  GAG  CTG  ACC     432
Arg  Glu  Pro  Gln  Val  Tyr  Thr  Leu  Pro  Pro  Ser  Arg  Asp  Glu  Leu  Thr
130                     135                     140

AAG  AAC  CAG  GTC  AGC  CTG  ACC  TGC  CTG  GTC  AAA  GGC  TTC  TAT  CCC  AGG     480
Lys  Asn  Gln  Val  Ser  Leu  Thr  Cys  Leu  Val  Lys  Gly  Phe  Tyr  Pro  Arg
145                     150                     155                     160

CAC  ATC  GCC  GTG  GAG  TGG  GAG  AGC  AAT  GGG  CAG  CCG  GAG  AAC  AAC  TAC     528
His  Ile  Ala  Val  Glu  Trp  Glu  Ser  Asn  Gly  Gln  Pro  Glu  Asn  Asn  Tyr
                     165                     170                     175

AAG  ACC  ACG  CCT  CCC  GTG  CTG  GAC  TCC  GAC  GGC  TCC  TTC  TTC  CTC  TAC     576
Lys  Thr  Thr  Pro  Pro  Val  Leu  Asp  Ser  Asp  Gly  Ser  Phe  Phe  Leu  Tyr
             180                     185                     190

AGC  AAG  CTC  ACC  GTG  GAC  AAG  AGC  AGG  TGG  CAG  CAG  GGG  AAC  GTC  TTC     624
Ser  Lys  Leu  Thr  Val  Asp  Lys  Ser  Arg  Trp  Gln  Gln  Gly  Asn  Val  Phe
        195                     200                     205

TCA  TGC  TCC  GTG  ATG  CAT  GAG  GCT  CTG  CAC  AAC  CAC  TAC  ACG  CAG  AAG     672
Ser  Cys  Ser  Val  Met  His  Glu  Ala  Leu  His  Asn  His  Tyr  Thr  Gln  Lys
210                     215                     220

AGC  CTC  TCC  CTG  TCT  CCG  GGT  AAA  TGAACTAGT                                   705
Ser  Leu  Ser  Leu  Ser  Pro  Gly  Lys
225                     230
```

( 2 ) INFORMATION FOR SEQ ID NO:4:

( i ) SEQUENCE CHARACTERISTICS:
        ( A ) LENGTH: 232 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Pro  Arg  Ser  Cys  Asp  Lys  Thr  His  Thr  Cys  Pro  Pro  Cys  Pro  Ala
 1                  5                        10                      15
Pro  Glu  Leu  Leu  Gly  Gly  Pro  Ser  Val  Phe  Leu  Phe  Pro  Pro  Lys  Pro
               20                       25                      30
Lys  Asp  Thr  Leu  Met  Ile  Ser  Arg  Thr  Pro  Glu  Val  Thr  Cys  Val  Val
          35                       40                      45
Val  Asp  Val  Ser  His  Glu  Asp  Pro  Glu  Val  Lys  Phe  Asn  Trp  Tyr  Val
     50                       55                      60
Asp  Gly  Val  Glu  Val  His  Asn  Ala  Lys  Thr  Lys  Pro  Arg  Glu  Glu  Gln
65                       70                      75                           80
Tyr  Asn  Ser  Thr  Tyr  Arg  Val  Val  Ser  Val  Leu  Thr  Val  Leu  His  Gln
                    85                       90                      95
Asp  Trp  Leu  Asn  Gly  Lys  Asp  Tyr  Lys  Cys  Lys  Val  Ser  Asn  Lys  Ala
               100                      105                     110
Leu  Pro  Ala  Pro  Met  Gln  Lys  Thr  Ile  Ser  Lys  Ala  Lys  Gly  Gln  Pro
          115                      120                     125
Arg  Glu  Pro  Gln  Val  Tyr  Thr  Leu  Pro  Pro  Ser  Arg  Asp  Glu  Leu  Thr
     130                      135                     140
Lys  Asn  Gln  Val  Ser  Leu  Thr  Cys  Leu  Val  Lys  Gly  Phe  Tyr  Pro  Arg
145                      150                     155                          160
His  Ile  Ala  Val  Glu  Trp  Glu  Ser  Asn  Gly  Gln  Pro  Glu  Asn  Asn  Tyr
                    165                      170                     175
Lys  Thr  Thr  Pro  Pro  Val  Leu  Asp  Ser  Asp  Gly  Ser  Phe  Phe  Leu  Tyr
               180                      185                     190
Ser  Lys  Leu  Thr  Val  Asp  Lys  Ser  Arg  Trp  Gln  Gln  Gly  Asn  Val  Phe
          195                      200                     205
Ser  Cys  Ser  Val  Met  His  Glu  Ala  Leu  His  Asn  His  Tyr  Thr  Gln  Lys
     210                      215                     220
Ser  Leu  Ser  Leu  Ser  Pro  Gly  Lys
225                      230
```

( 2 ) INFORMATION FOR SEQ ID NO:5:

( i ) SEQUENCE CHARACTERISTICS:
        ( A ) LENGTH: 4171 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: huOSM-Ra ( i x ) FEATURE:
        ( A ) NAME/KEY: sig_peptide
        ( B ) LOCATION: 368..448

( i x ) FEATURE:
    ( A ) NAME/KEY: CDS
    ( B ) LOCATION: 368..3307

( i x ) FEATURE:
    ( A ) NAME/KEY: mat_peptide
    ( B ) LOCATION: 449..3304

( x i ) SEQUENCE DESCRIPTION: SEQ ID NO:5:

```
GGGCCGCCTC TGCACGTCCG CCCCGGAGCC CGCACCCGCG CCCCACGCGC CGCCGAGGAC      60

TCGGCCCGGC TCGTGGAGCC CTTCGCCCGC GGCGTGAGTA CCCCCGACCC GCCCGTCCCC     120

GCTCTGCTCG CGCCCTGCCG CTGCGCCGCC CTCGGTGGCT TTTCCGACGG GCGAGCCCCG     180

TGCTGTGCGG GAAAGAATCC GACAACTTCG CAGCCCATCC CGGCTGGACG CGACCGGGAG     240

TGCAGCAGCC CGTTCCCCTC CTCGGTGCCG CCTCTGCCCA GCGTTTGCTT GGCTGGGCTA     300

CCACCTGCGC TCGGACGGCG CTCGGAGGGT CCTCGCCCCC GGCCTGCCTA CCTGAAAACC     360
```

| AGAACTG | ATG | GCT | CTA | TTT | GCA | GTC | TTT | CAG | ACA | ACA | TTC | TTC | TTA | ACA | 409 |
|---|---|---|---|---|---|---|---|---|---|---|---|---|---|---|---|
| | Met | Ala | Leu | Phe | Ala | Val | Phe | Gln | Thr | Thr | Phe | Phe | Leu | Thr | |
| | -27 | | -25 | | | | | -20 | | | | | -15 | | |

| TTG | CTG | TCC | TTG | AGG | ACT | TAC | CAG | AGT | GAA | GTC | TTG | GCT | GAA | CGT | TTA | 457 |
|---|---|---|---|---|---|---|---|---|---|---|---|---|---|---|---|---|
| Leu | Leu | Ser | Leu | Arg | Thr | Tyr | Gln | Ser | Glu | Val | Leu | Ala | Glu | Arg | Leu | |
| | | | -10 | | | | | -5 | | | | | | 1 | | |

| CCA | TTG | ACT | CCT | GTA | TCA | CTT | AAA | GTT | TCC | ACC | AAT | TCT | ACG | CGT | CAG | 505 |
|---|---|---|---|---|---|---|---|---|---|---|---|---|---|---|---|---|
| Pro | Leu | Thr | Pro | Val | Ser | Leu | Lys | Val | Ser | Thr | Asn | Ser | Thr | Arg | Gln | |
| | | 5 | | | | | 10 | | | | | 15 | | | | |

| AGT | TTG | CAC | TTA | CAA | TGG | ACT | GTC | CAC | AAC | CTT | CCT | TAT | CAT | CAG | GAA | 553 |
|---|---|---|---|---|---|---|---|---|---|---|---|---|---|---|---|---|
| Ser | Leu | His | Leu | Gln | Trp | Thr | Val | His | Asn | Leu | Pro | Tyr | His | Gln | Glu | |
| 20 | | | | | 25 | | | | | 30 | | | | | 35 | |

| TTG | AAA | ATG | GTA | TTT | CAG | ATC | CAG | ATC | AGT | AGG | ATT | GAA | ACA | TCC | AAT | 601 |
|---|---|---|---|---|---|---|---|---|---|---|---|---|---|---|---|---|
| Leu | Lys | Met | Val | Phe | Gln | Ile | Gln | Ile | Ser | Arg | Ile | Glu | Thr | Ser | Asn | |
| | | | | 40 | | | | | 45 | | | | | 50 | | |

| GTC | ATC | TGG | GTG | GGG | AAT | TAC | AGC | ACC | ACT | GTG | AAG | TGG | AAC | CAG | GTT | 649 |
|---|---|---|---|---|---|---|---|---|---|---|---|---|---|---|---|---|
| Val | Ile | Trp | Val | Gly | Asn | Tyr | Ser | Thr | Thr | Val | Lys | Trp | Asn | Gln | Val | |
| | | | | 55 | | | | | 60 | | | | | 65 | | |

| CTG | CAT | TGG | AGC | TGG | GAA | TCT | GAG | CTC | CCT | TTG | GAA | TGT | GCC | ACA | CAC | 697 |
|---|---|---|---|---|---|---|---|---|---|---|---|---|---|---|---|---|
| Leu | His | Trp | Ser | Trp | Glu | Ser | Glu | Leu | Pro | Leu | Glu | Cys | Ala | Thr | His | |
| | | 70 | | | | | 75 | | | | | 80 | | | | |

| TTT | GTA | AGA | ATA | AAG | AGT | TTG | GTG | GAC | GAT | GCC | AAG | TTC | CCT | GAG | CCA | 745 |
|---|---|---|---|---|---|---|---|---|---|---|---|---|---|---|---|---|
| Phe | Val | Arg | Ile | Lys | Ser | Leu | Val | Asp | Asp | Ala | Lys | Phe | Pro | Glu | Pro | |
| | | 85 | | | | | 90 | | | | | 95 | | | | |

| AAT | TTC | TGG | AGC | AAC | TGG | AGT | TCC | TGG | GAG | GAA | GTC | AGT | GTA | CAA | GAT | 793 |
|---|---|---|---|---|---|---|---|---|---|---|---|---|---|---|---|---|
| Asn | Phe | Trp | Ser | Asn | Trp | Ser | Ser | Trp | Glu | Glu | Val | Ser | Val | Gln | Asp | |
| 100 | | | | | 105 | | | | | 110 | | | | | 115 | |

| TCT | ACT | GGA | CAG | GAT | ATA | TTG | TTC | GTT | TTC | CCT | AAA | GAT | AAG | CTG | GTG | 841 |
|---|---|---|---|---|---|---|---|---|---|---|---|---|---|---|---|---|
| Ser | Thr | Gly | Gln | Asp | Ile | Leu | Phe | Val | Phe | Pro | Lys | Asp | Lys | Leu | Val | |
| | | | | 120 | | | | | 125 | | | | | 130 | | |

| GAA | GAA | GGC | ACC | AAT | GTT | ACC | ATT | TGT | TAC | GTT | TCT | AGG | AAC | ATT | CAA | 889 |
|---|---|---|---|---|---|---|---|---|---|---|---|---|---|---|---|---|
| Glu | Glu | Gly | Thr | Asn | Val | Thr | Ile | Cys | Tyr | Val | Ser | Arg | Asn | Ile | Gln | |
| | | 135 | | | | | 140 | | | | | 145 | | | | |

| AAT | AAT | GTA | TCC | TGT | TAT | TTG | GAA | GGG | AAA | CAG | ATT | CAT | GGA | GAA | CAA | 937 |
|---|---|---|---|---|---|---|---|---|---|---|---|---|---|---|---|---|
| Asn | Asn | Val | Ser | Cys | Tyr | Leu | Glu | Gly | Lys | Gln | Ile | His | Gly | Glu | Gln | |
| | | 150 | | | | | 155 | | | | | 160 | | | | |

| CTT | GAT | CCA | CAT | GTA | ACT | GCA | TTC | AAC | TTG | AAT | AGT | GTG | CCT | TTC | ATT | 985 |
|---|---|---|---|---|---|---|---|---|---|---|---|---|---|---|---|---|
| Leu | Asp | Pro | His | Val | Thr | Ala | Phe | Asn | Leu | Asn | Ser | Val | Pro | Phe | Ile | |
| 165 | | | | | 170 | | | | | 175 | | | | | | |

| AGG | AAT | AAA | GGG | ACA | AAT | ATC | TAT | TGT | GAG | GCA | AGT | CAA | GGA | AAT | GTC | 1033 |
|---|---|---|---|---|---|---|---|---|---|---|---|---|---|---|---|---|
| Arg | Asn | Lys | Gly | Thr | Asn | Ile | Tyr | Cys | Glu | Ala | Ser | Gln | Gly | Asn | Val | |
| 180 | | | | | 185 | | | | | 190 | | | | | 195 | |

| AGT | GAA | GGC | ATG | AAA | GGC | ATC | GTT | CTT | TTT | GTC | TCA | AAA | GTA | CTT | GAG | 1081 |
|---|---|---|---|---|---|---|---|---|---|---|---|---|---|---|---|---|
| Ser | Glu | Gly | Met | Lys | Gly | Ile | Val | Leu | Phe | Val | Ser | Lys | Val | Leu | Glu | |

|     |     |     |     |     |     | 200 |     |     |     |     | 205 |     |     |     |     | 210 |     |      |
| --- | --- | --- | --- | --- | --- | --- | --- | --- | --- | --- | --- | --- | --- | --- | --- | --- | --- | ---- |
| GAG | CCC | AAG | GAC | TTT | TCT | TGT | GAA | ACC | GAG | GAC | TTC | AAG | ACT | TTG | CAC |     |     | 1129 |
| Glu | Pro | Lys | Asp | Phe | Ser | Cys | Glu | Thr | Glu | Asp | Phe | Lys | Thr | Leu | His |     |     |      |
|     |     |     | 215 |     |     |     |     | 220 |     |     |     |     | 225 |     |     |     |     |      |
| TGT | ACT | TGG | GAT | CCT | GGG | ACG | GAC | ACT | GCC | TTG | GGG | TGG | TCT | AAA | CAA |     |     | 1177 |
| Cys | Thr | Trp | Asp | Pro | Gly | Thr | Asp | Thr | Ala | Leu | Gly | Trp | Ser | Lys | Gln |     |     |      |
|     |     | 230 |     |     |     |     | 235 |     |     |     |     | 240 |     |     |     |     |     |      |
| CCT | TCC | CAA | AGC | TAC | ACT | TTA | TTT | GAA | TCA | TTT | TCT | GGG | GAA | AAG | AAA |     |     | 1225 |
| Pro | Ser | Gln | Ser | Tyr | Thr | Leu | Phe | Glu | Ser | Phe | Ser | Gly | Glu | Lys | Lys |     |     |      |
|     | 245 |     |     |     |     | 250 |     |     |     |     | 255 |     |     |     |     |     |     |      |
| CTT | TGT | ACA | CAC | AAA | AAC | TGG | TGT | AAT | TGG | CAA | ATA | ACT | CAA | GAC | TCA |     |     | 1273 |
| Leu | Cys | Thr | His | Lys | Asn | Trp | Cys | Asn | Trp | Gln | Ile | Thr | Gln | Asp | Ser |     |     |      |
| 260 |     |     |     |     | 265 |     |     |     |     | 270 |     |     |     |     | 275 |     |     |      |
| CAA | GAA | ACC | TAT | AAC | TTC | ACA | CTC | ATA | GCT | GAA | AAT | TAC | TTA | AGG | AAG |     |     | 1321 |
| Gln | Glu | Thr | Tyr | Asn | Phe | Thr | Leu | Ile | Ala | Glu | Asn | Tyr | Leu | Arg | Lys |     |     |      |
|     |     |     |     | 280 |     |     |     |     | 285 |     |     |     |     | 290 |     |     |     |      |
| AGA | AGT | GTC | AAT | ATC | CTT | TTT | AAC | CTG | ACT | CAT | CGA | GTT | TAT | TTA | ATG |     |     | 1369 |
| Arg | Ser | Val | Asn | Ile | Leu | Phe | Asn | Leu | Thr | His | Arg | Val | Tyr | Leu | Met |     |     |      |
|     |     |     | 295 |     |     |     |     | 300 |     |     |     |     | 305 |     |     |     |     |      |
| AAT | CCT | TTT | AGT | GTC | AAC | TTT | GAA | AAT | GTA | AAT | GCC | ACA | AAT | GCC | ATC |     |     | 1417 |
| Asn | Pro | Phe | Ser | Val | Asn | Phe | Glu | Asn | Val | Asn | Ala | Thr | Asn | Ala | Ile |     |     |      |
|     |     | 310 |     |     |     |     | 315 |     |     |     |     | 320 |     |     |     |     |     |      |
| ATG | ACC | TGG | AAG | GTG | CAC | TCC | ATA | AGG | AAT | AAT | TTC | ACA | TAT | TTG | TGT |     |     | 1465 |
| Met | Thr | Trp | Lys | Val | His | Ser | Ile | Arg | Asn | Asn | Phe | Thr | Tyr | Leu | Cys |     |     |      |
| 325 |     |     |     |     | 330 |     |     |     |     | 335 |     |     |     |     |     |     |     |      |
| CAG | ATT | GAA | CTC | CAT | GGT | GAA | GGA | AAA | ATG | ATG | CAA | TAC | AAT | GTT | TCC |     |     | 1513 |
| Gln | Ile | Glu | Leu | His | Gly | Glu | Gly | Lys | Met | Met | Gln | Tyr | Asn | Val | Ser |     |     |      |
| 340 |     |     |     |     | 345 |     |     |     |     | 350 |     |     |     |     | 355 |     |     |      |
| ATC | AAG | GTG | AAC | GGT | GAG | TAC | TTC | TTA | AGT | GAA | CTG | GAA | CCT | GCC | ACA |     |     | 1561 |
| Ile | Lys | Val | Asn | Gly | Glu | Tyr | Phe | Leu | Ser | Glu | Leu | Glu | Pro | Ala | Thr |     |     |      |
|     |     |     |     | 360 |     |     |     |     | 365 |     |     |     |     | 370 |     |     |     |      |
| GAG | TAC | ATG | GCG | CGA | GTA | CGG | TGT | GCT | GAT | GCC | AGC | CAC | TTC | TGG | AAA |     |     | 1609 |
| Glu | Tyr | Met | Ala | Arg | Val | Arg | Cys | Ala | Asp | Ala | Ser | His | Phe | Trp | Lys |     |     |      |
|     |     |     | 375 |     |     |     |     | 380 |     |     |     |     | 385 |     |     |     |     |      |
| TGG | AGT | GAA | TGG | AGT | GGT | CAG | AAC | TTC | ACC | ACA | CTT | GAA | GCT | GCT | CCC |     |     | 1657 |
| Trp | Ser | Glu | Trp | Ser | Gly | Gln | Asn | Phe | Thr | Thr | Leu | Glu | Ala | Ala | Pro |     |     |      |
|     |     | 390 |     |     |     |     | 395 |     |     |     |     | 400 |     |     |     |     |     |      |
| TCA | GAG | GCC | CCT | GAT | GTC | TGG | AGA | ATT | GTG | AGC | TTG | GAG | CCA | GGA | AAT |     |     | 1705 |
| Ser | Glu | Ala | Pro | Asp | Val | Trp | Arg | Ile | Val | Ser | Leu | Glu | Pro | Gly | Asn |     |     |      |
|     | 405 |     |     |     |     | 410 |     |     |     |     | 415 |     |     |     |     |     |     |      |
| CAT | ACT | GTG | ACC | TTA | TTC | TGG | AAG | CCA | TTA | TCA | AAA | CTG | CAT | GCC | AAT |     |     | 1753 |
| His | Thr | Val | Thr | Leu | Phe | Trp | Lys | Pro | Leu | Ser | Lys | Leu | His | Ala | Asn |     |     |      |
| 420 |     |     |     |     | 425 |     |     |     |     | 430 |     |     |     |     | 435 |     |     |      |
| GGA | AAG | ATC | CTG | TTC | TAT | AAT | GTA | GTT | GTA | GAA | AAC | CTA | GAC | AAA | CCA |     |     | 1801 |
| Gly | Lys | Ile | Leu | Phe | Tyr | Asn | Val | Val | Val | Glu | Asn | Leu | Asp | Lys | Pro |     |     |      |
|     |     |     |     | 440 |     |     |     |     | 445 |     |     |     |     | 450 |     |     |     |      |
| TCC | AGT | TCA | GAG | CTC | CAT | TCC | ATT | CCA | GCA | CCA | GCC | AAC | AGC | ACA | AAA |     |     | 1849 |
| Ser | Ser | Ser | Glu | Leu | His | Ser | Ile | Pro | Ala | Pro | Ala | Asn | Ser | Thr | Lys |     |     |      |
|     |     |     | 455 |     |     |     |     | 460 |     |     |     |     | 465 |     |     |     |     |      |
| CTA | ATC | CTT | GAC | AGG | TGT | TCC | TAC | CAA | ATC | TGC | GTC | ATA | GCC | AAC | AAC |     |     | 1897 |
| Leu | Ile | Leu | Asp | Arg | Cys | Ser | Tyr | Gln | Ile | Cys | Val | Ile | Ala | Asn | Asn |     |     |      |
|     |     |     | 470 |     |     |     |     | 475 |     |     |     |     | 480 |     |     |     |     |      |
| AGT | GTG | GGT | GCT | TCT | CCT | GCT | TCT | GTA | ATA | GTC | ATC | TCT | GCA | GAC | CCC |     |     | 1945 |
| Ser | Val | Gly | Ala | Ser | Pro | Ala | Ser | Val | Ile | Val | Ile | Ser | Ala | Asp | Pro |     |     |      |
|     | 485 |     |     |     |     | 490 |     |     |     |     | 495 |     |     |     |     |     |     |      |
| GAA | AAC | AAA | GAG | GTT | GAG | GAA | GAA | AGA | ATT | GCA | GGC | ACA | GAG | GGT | GGA |     |     | 1993 |
| Glu | Asn | Lys | Glu | Val | Glu | Glu | Glu | Arg | Ile | Ala | Gly | Thr | Glu | Gly | Gly |     |     |      |
| 500 |     |     |     |     | 505 |     |     |     |     | 510 |     |     |     |     | 515 |     |     |      |
| TTC | TCT | CTG | TCT | TGG | AAA | CCC | CAA | CCT | GGA | GAT | GTT | ATA | GGC | TAT | GTT |     |     | 2041 |
| Phe | Ser | Leu | Ser | Trp | Lys | Pro | Gln | Pro | Gly | Asp | Val | Ile | Gly | Tyr | Val |     |     |      |

-continued

| | | | | | | | | | | | | | | | | |
|---|---|---|---|---|---|---|---|---|---|---|---|---|---|---|---|---|
| | | | | 520 | | | | | 525 | | | | | 530 | | |
| GTG | GAC | TGG | TGT | GAC | CAT | ACC | CAG | GAT | GTG | CTC | GGT | GAT | TTC | CAG | TGG | 2089 |
| Val | Asp | Trp | Cys 535 | Asp | His | Thr | Gln 540 | Asp | Val | Leu | Gly | Asp 545 | Phe | Gln | Trp | |
| AAG | AAT | GTA | GGT | CCC | AAT | ACC | ACA | AGC | ACA | GTC | ATT | AGC | ACA | GAT | GCT | 2137 |
| Lys | Asn | Val 550 | Gly | Pro | Asn | Thr | Thr 555 | Ser | Thr | Val | Ile | Ser 560 | Thr | Asp | Ala | |
| TTT | AGG | CCA | GGA | GTT | CGA | TAT | GAC | TTC | AGA | ATT | TAT | GGG | TTA | TCT | ACA | 2185 |
| Phe | Arg 565 | Pro | Gly | Val | Arg | Tyr 570 | Asp | Phe | Arg | Ile | Tyr 575 | Gly | Leu | Ser | Thr | |
| AAA | AGG | ATT | GCT | TGT | TTA | TTA | GAG | AAA | AAA | ACA | GGA | TAC | TCT | CAG | GAA | 2233 |
| Lys 580 | Arg | Ile | Ala | Cys 585 | Leu | Leu | Glu | Lys | Lys 590 | Thr | Gly | Tyr | Ser | Gln 595 | Glu | |
| CTT | GCT | CCT | TCA | GAC | AAC | CCT | CAC | GTG | CTG | GTG | GAT | ACA | TTG | ACA | TCC | 2281 |
| Leu | Ala | Pro | Ser | Asp 600 | Asn | Pro | His | Val | Leu 605 | Val | Asp | Thr | Leu | Thr 610 | Ser | |
| CAC | TCC | TTC | ACT | CTG | AGT | TGG | AAA | GAT | TAC | TCT | ACT | GAA | TCT | CAA | CCT | 2329 |
| His | Ser | Phe | Thr 615 | Leu | Ser | Trp | Lys | Asp 620 | Tyr | Ser | Thr | Glu | Ser 625 | Gln | Pro | |
| GGT | TTT | ATA | CAA | GGG | TAC | CAT | GTC | TAT | CTG | AAA | TCC | AAG | GCG | AGG | CAG | 2377 |
| Gly | Phe | Ile 630 | Gln | Gly | Tyr | His | Val 635 | Tyr | Leu | Lys | Ser | Lys 640 | Ala | Arg | Gln | |
| TGC | CAC | CCA | CGA | TTT | GAA | AAG | GCA | GTT | CTT | TCA | GAT | GGT | TCA | GAA | TGT | 2425 |
| Cys | His 645 | Pro | Arg | Phe | Glu | Lys 650 | Ala | Val | Leu | Ser | Asp 655 | Gly | Ser | Glu | Cys | |
| TGC | AAA | TAC | AAA | ATT | GAC | AAC | CCG | GAA | GAA | AAG | GCA | TTG | ATT | GTG | GAC | 2473 |
| Cys 660 | Lys | Tyr | Lys | Ile | Asp 665 | Asn | Pro | Glu | Glu | Lys 670 | Ala | Leu | Ile | Val | Asp 675 | |
| AAC | CTA | AAG | CCA | GAA | TCC | TTC | TAT | GAG | TTT | TTC | ATC | ACT | CCA | TTC | ACT | 2521 |
| Asn | Leu | Lys | Pro | Glu 680 | Ser | Phe | Tyr | Glu | Phe 685 | Phe | Ile | Thr | Pro | Phe 690 | Thr | |
| AGT | GCT | GGT | GAA | GGC | CCC | AGT | GCT | ACG | TTC | ACG | AAG | GTC | ACG | ACT | CCG | 2569 |
| Ser | Ala | Gly | Glu 695 | Gly | Pro | Ser | Ala | Thr 700 | Phe | Thr | Lys | Val | Thr 705 | Thr | Pro | |
| GAT | GAA | CAC | TCC | TCG | ATG | CTG | ATT | CAT | ATC | CTA | CTG | CCC | ATG | GTT | TTC | 2617 |
| Asp | Glu | His | Ser 710 | Ser | Met | Leu | Ile | His 715 | Ile | Leu | Leu | Pro | Met 720 | Val | Phe | |
| TGC | GTC | TTG | CTC | ATC | ATG | GTC | ATG | TGC | TAC | TTG | AAA | AGT | CAG | TGG | ATC | 2665 |
| Cys | Val | Leu 725 | Leu | Ile | Met | Val | Met 730 | Cys | Tyr | Leu | Lys | Ser 735 | Gln | Trp | Ile | |
| AAG | GAG | ACC | TGT | TAT | CCT | GAC | ATC | CCT | GAC | CCT | TAC | AAG | AGC | AGC | ATC | 2713 |
| Lys 740 | Glu | Thr | Cys | Tyr | Pro 745 | Asp | Ile | Pro | Asp | Pro 750 | Tyr | Lys | Ser | Ser | Ile 755 | |
| CTG | TCA | TTA | ATA | AAA | TTC | AAG | GAG | AAC | CCT | CAC | CTA | ATA | ATA | ATG | AAT | 2761 |
| Leu | Ser | Leu | Ile | Lys 760 | Phe | Lys | Glu | Asn | Pro 765 | His | Leu | Ile | Ile | Met 770 | Asn | |
| GTC | AGT | GAC | TGT | ATC | CCA | GAT | GCT | ATT | GAA | GTT | GTA | AGC | AAG | CCA | GAA | 2809 |
| Val | Ser | Asp | Cys 775 | Ile | Pro | Asp | Ala | Ile 780 | Glu | Val | Val | Ser | Lys 785 | Pro | Glu | |
| GGG | ACA | AAG | ATA | CAG | TTC | CTA | GGC | ACT | AGG | AAG | TCA | CTC | ACA | GAA | ACC | 2857 |
| Gly | Thr | Lys 790 | Ile | Gln | Phe | Leu | Gly 795 | Thr | Arg | Lys | Ser | Leu 800 | Thr | Glu | Thr | |
| GAG | TTG | ACT | AAG | CCT | AAC | TAC | CTT | TAT | CTC | CTT | CCA | ACA | GAA | AAG | AAT | 2905 |
| Glu | Leu | Thr 805 | Lys | Pro | Asn | Tyr | Leu 810 | Tyr | Leu | Leu | Pro | Thr 815 | Glu | Lys | Asn | |
| CAC | TCT | GGC | CCT | GGC | CCC | TGC | ATC | TGT | TTT | GAG | AAC | TTG | ACC | TAT | AAC | 2953 |
| His | Ser | Gly | Pro 820 | Gly | Pro | Cys | Ile | Cys 825 | Phe | Glu | Asn | Leu | Thr 830 | Tyr | Asn 835 | |
| CAG | GCA | GCT | TCT | GAC | TCT | GGC | TCT | TGT | GGC | CAT | GTT | CCA | GTA | TCC | CCA | 3001 |
| Gln | Ala | Ala | Ser | Asp | Ser | Gly | Ser | Cys | Gly | His | Val | Pro | Val | Ser | Pro | |

-continued

|  |  |  | 840 |  |  |  | 845 |  |  |  | 850 |  |  |  |
|---|---|---|---|---|---|---|---|---|---|---|---|---|---|---|
| AAA | GCC | CCA | AGT | ATG | CTG | GGA | CTA | ATG | ACC | TCA | CCT | GAA | AAT | GTA | CTA | 3049 |
| Lys | Ala | Pro | Ser | Met | Leu | Gly | Leu | Met | Thr | Ser | Pro | Glu | Asn | Val | Leu |
|  |  |  | 855 |  |  |  | 860 |  |  |  | 865 |  |  |  |

```
AAA GCC CCA AGT ATG CTG GGA CTA ATG ACC TCA CCT GAA AAT GTA CTA      3049
Lys Ala Pro Ser Met Leu Gly Leu Met Thr Ser Pro Glu Asn Val Leu
            855                 860                 865

AAG GCA CTA GAA AAA AAC TAC ATG AAC TCC CTG GGA GAA ATC CCA GCT      3097
Lys Ala Leu Glu Lys Asn Tyr Met Asn Ser Leu Gly Glu Ile Pro Ala
            870                 875                 880

GGA GAA ACA AGT TTG AAT TAT GTG TCC CAG TTG GCT TCA CCC ATG TTT      3145
Gly Glu Thr Ser Leu Asn Tyr Val Ser Gln Leu Ala Ser Pro Met Phe
            885                 890                 895

GGA GAC AAG GAC AGT CTC CCA ACA AAC CCA GTA GAG GCA CCA CAC TGT      3193
Gly Asp Lys Asp Ser Leu Pro Thr Asn Pro Val Glu Ala Pro His Cys
900             905                 910                 915

TCA GAG TAT AAA ATG CAA ATG GCA GTC TCC CTG CGT CTT GCC TTG CCT      3241
Ser Glu Tyr Lys Met Gln Met Ala Val Ser Leu Arg Leu Ala Leu Pro
            920                 925                 930

CCC CCG ACC GAG AAT AGC AGC CTC TCC TCA ATT ACC CTT TTA GAT CCA      3289
Pro Pro Thr Glu Asn Ser Ser Leu Ser Ser Ile Thr Leu Leu Asp Pro
            935                 940                 945

GGT GAA CAC TAC TGC TAACCAGCAT GCCGATTTCA TACCTTATGC TACACAGACA       3344
Gly Glu His Tyr Cys
            950

TTAAGAAGAG CAGAGCTGGC ACCCTGTCAT CACCAGTGGC CTTGGTCCTT AATCCCAGTA    3404

CAATTTGCAG GTCTGGTTTA TATAAGACCA CTACAGTCTG GCTAGGTTAA AGGCCAGAGG    3464

CTATGGAACT TAACACTCCC CATTGGAGCA AGCTTGCCCT AGAGACGGCA GGATCATGGG    3524

AGCATGCTTA CCTTCTGCTG TTTGTTCCAG GCTCACCTTT AGAACAGGAG ACTTGAGCTT    3584

GACCTAAGGA TATGCATTAA CCACTCTACA GACTCCCACT CAGTACTGTA CAGGGTGGCT    3644

GTGGTCCTAG AAGTTCAGTT TTTACTGAGG AAATATTTCC ATTAACAGCA ATTATTATAT    3704

TGAAGGCTTT AATAAAGGCC ACAGGAGACA TTACTATAGC ATAGATTGTC AAATGTAAAT    3764

TTACTGAGCG TGTTTTATAA AAAACTCACA GGTGTTTGAG GCCAAAACAG ATTTTAGACT    3824

TACCTTGAAC GGATAAGAAT CTATAGTTCA CTGACACAGT AAAATTAACT CTGTGGGTGG    3884

GGGCGGGGGG CATAGCTCTA ATCTAATATA TAAAATGTGT GATGAATCAA CAAGATTTCC    3944

ACAATTCTTC TGTCAAGCTT ACTACAGTGA AAGAATGGGA TTGGCAAGTA ACTTCTGACT    4004

TACTGTCAGT TGTACTTCTG CTCCATAGAC ATCAGTATTC TGCCATCATT TTTGATGACT    4064

ACCTCAGAAC ATAAAAGGA ACGTATATCA CATAATTCCA GTCACAGTTT TGGTTCCTC     4124

TTTTCTTTCA AGAACTATAT ATAAATGACC TGTTTTCACG CGGCCGC                  4171
```

( 2 ) INFORMATION FOR SEQ ID NO:6:

( i ) SEQUENCE CHARACTERISTICS:
        ( A ) LENGTH: 979 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Leu Phe Ala Val Phe Gln Thr Thr Phe Phe Leu Thr Leu Leu
-27         -25                 -20                 -15

Ser Leu Arg Thr Tyr Gln Ser Glu Val Leu Ala Glu Arg Leu Pro Leu
        -10                 -5                  1               5

Thr Pro Val Ser Leu Lys Val Ser Thr Asn Ser Thr Arg Gln Ser Leu
                    10                  15                  20

His Leu Gln Trp Thr Val His Asn Leu Pro Tyr His Gln Glu Leu Lys
```

|  | 25 |  |  |  |  | 30 |  |  |  |  | 35 |  |  |
|---|---|---|---|---|---|---|---|---|---|---|---|---|---|
| Met | Val | Phe | Gln | Ile | Gln | Ile | Ser | Arg | Ile | Glu | Thr | Ser | Asn | Val | Ile |
|  |  | 40 |  |  |  | 45 |  |  |  |  | 50 |  |  |

| Trp | Val | Gly | Asn | Tyr | Ser | Thr | Thr | Val | Lys | Trp | Asn | Gln | Val | Leu | His |
|  | 55 |  |  |  |  | 60 |  |  |  |  | 65 |  |  |  |  |

| Trp | Ser | Trp | Glu | Ser | Glu | Leu | Pro | Leu | Glu | Cys | Ala | Thr | His | Phe | Val |
| 70 |  |  |  |  | 75 |  |  |  |  | 80 |  |  |  |  | 85 |

| Arg | Ile | Lys | Ser | Leu | Val | Asp | Asp | Ala | Lys | Phe | Pro | Glu | Pro | Asn | Phe |
|  |  |  |  | 90 |  |  |  |  | 95 |  |  |  |  | 100 |  |

| Trp | Ser | Asn | Trp | Ser | Ser | Trp | Glu | Glu | Val | Ser | Val | Gln | Asp | Ser | Thr |
|  |  |  | 105 |  |  |  |  | 110 |  |  |  |  | 115 |  |  |

| Gly | Gln | Asp | Ile | Leu | Phe | Val | Phe | Pro | Lys | Asp | Lys | Leu | Val | Glu | Glu |
|  |  | 120 |  |  |  |  | 125 |  |  |  |  | 130 |  |  |  |

| Gly | Thr | Asn | Val | Thr | Ile | Cys | Tyr | Val | Ser | Arg | Asn | Ile | Gln | Asn | Asn |
|  | 135 |  |  |  |  | 140 |  |  |  |  | 145 |  |  |  |  |

| Val | Ser | Cys | Tyr | Leu | Glu | Gly | Lys | Gln | Ile | His | Gly | Glu | Gln | Leu | Asp |
| 150 |  |  |  |  | 155 |  |  |  |  | 160 |  |  |  |  | 165 |

| Pro | His | Val | Thr | Ala | Phe | Asn | Leu | Asn | Ser | Val | Pro | Phe | Ile | Arg | Asn |
|  |  |  |  | 170 |  |  |  |  | 175 |  |  |  |  | 180 |  |

| Lys | Gly | Thr | Asn | Ile | Tyr | Cys | Glu | Ala | Ser | Gln | Gly | Asn | Val | Ser | Glu |
|  |  |  | 185 |  |  |  |  | 190 |  |  |  |  | 195 |  |  |

| Gly | Met | Lys | Gly | Ile | Val | Leu | Phe | Val | Ser | Lys | Val | Leu | Glu | Glu | Pro |
|  |  | 200 |  |  |  |  | 205 |  |  |  |  | 210 |  |  |  |

| Lys | Asp | Phe | Ser | Cys | Glu | Thr | Glu | Asp | Phe | Lys | Thr | Leu | His | Cys | Thr |
|  | 215 |  |  |  |  | 220 |  |  |  |  | 225 |  |  |  |  |

| Trp | Asp | Pro | Gly | Thr | Asp | Thr | Ala | Leu | Gly | Trp | Ser | Lys | Gln | Pro | Ser |
| 230 |  |  |  |  | 235 |  |  |  |  | 240 |  |  |  |  | 245 |

| Gln | Ser | Tyr | Thr | Leu | Phe | Glu | Ser | Phe | Ser | Gly | Glu | Lys | Lys | Leu | Cys |
|  |  |  |  | 250 |  |  |  |  | 255 |  |  |  |  | 260 |  |

| Thr | His | Lys | Asn | Trp | Cys | Asn | Trp | Gln | Ile | Thr | Gln | Asp | Ser | Gln | Glu |
|  |  |  | 265 |  |  |  |  | 270 |  |  |  |  | 275 |  |  |

| Thr | Tyr | Asn | Phe | Thr | Leu | Ile | Ala | Glu | Asn | Tyr | Leu | Arg | Lys | Arg | Ser |
|  |  | 280 |  |  |  |  | 285 |  |  |  |  | 290 |  |  |  |

| Val | Asn | Ile | Leu | Phe | Asn | Leu | Thr | His | Arg | Val | Tyr | Leu | Met | Asn | Pro |
|  | 295 |  |  |  |  | 300 |  |  |  |  | 305 |  |  |  |  |

| Phe | Ser | Val | Asn | Phe | Glu | Asn | Val | Asn | Ala | Thr | Asn | Ala | Ile | Met | Thr |
| 310 |  |  |  |  | 315 |  |  |  |  | 320 |  |  |  |  | 325 |

| Trp | Lys | Val | His | Ser | Ile | Arg | Asn | Asn | Phe | Thr | Tyr | Leu | Cys | Gln | Ile |
|  |  |  | 330 |  |  |  |  | 335 |  |  |  |  | 340 |  |  |

| Glu | Leu | His | Gly | Glu | Gly | Lys | Met | Met | Gln | Tyr | Asn | Val | Ser | Ile | Lys |
|  |  |  | 345 |  |  |  |  | 350 |  |  |  |  | 355 |  |  |

| Val | Asn | Gly | Glu | Tyr | Phe | Leu | Ser | Glu | Leu | Glu | Pro | Ala | Thr | Glu | Tyr |
|  |  | 360 |  |  |  |  | 365 |  |  |  |  | 370 |  |  |  |

| Met | Ala | Arg | Val | Arg | Cys | Ala | Asp | Ala | Ser | His | Phe | Trp | Lys | Trp | Ser |
|  | 375 |  |  |  |  | 380 |  |  |  |  | 385 |  |  |  |  |

| Glu | Trp | Ser | Gly | Gln | Asn | Phe | Thr | Thr | Leu | Glu | Ala | Ala | Pro | Ser | Glu |
| 390 |  |  |  |  | 395 |  |  |  |  | 400 |  |  |  |  | 405 |

| Ala | Pro | Asp | Val | Trp | Arg | Ile | Val | Ser | Leu | Glu | Pro | Gly | Asn | His | Thr |
|  |  |  |  | 410 |  |  |  |  | 415 |  |  |  |  | 420 |  |

| Val | Thr | Leu | Phe | Trp | Lys | Pro | Leu | Ser | Lys | Leu | His | Ala | Asn | Gly | Lys |
|  |  |  | 425 |  |  |  |  | 430 |  |  |  |  | 435 |  |  |

| Ile | Leu | Phe | Tyr | Asn | Val | Val | Val | Glu | Asn | Leu | Asp | Lys | Pro | Ser | Ser |
|  |  | 440 |  |  |  |  | 445 |  |  |  |  | 450 |  |  |  |

-continued

| | | | | | | | | | | | | | |
|---|---|---|---|---|---|---|---|---|---|---|---|---|---|
| Ser | Glu 455 | Leu | His | Ser | Ile 460 | Pro | Ala | Pro | Ala | Asn 465 | Ser | Thr | Lys | Leu | Ile |
| Leu 470 | Asp | Arg | Cys | Ser | Tyr 475 | Gln | Ile | Cys | Val | Ile 480 | Ala | Asn | Asn | Ser | Val 485 |
| Gly | Ala | Ser | Pro | Ala 490 | Ser | Val | Ile | Val | Ile 495 | Ser | Ala | Asp | Pro | Asn 500 |
| Lys | Glu | Val | Glu | Glu 505 | Arg | Ile | Ala | Gly | Thr 510 | Glu | Gly | Gly | Phe 515 | Ser |
| Leu | Ser | Trp | Lys 520 | Pro | Gln | Pro | Gly | Asp 525 | Val | Ile | Gly | Tyr 530 | Val | Val | Asp |
| Trp | Cys 535 | Asp | His | Thr | Gln | Asp 540 | Val | Leu | Gly | Asp | Phe 545 | Gln | Trp | Lys | Asn |
| Val 550 | Gly | Pro | Asn | Thr | Thr 555 | Ser | Thr | Val | Ile | Ser 560 | Thr | Asp | Ala | Phe | Arg 565 |
| Pro | Gly | Val | Arg | Tyr 570 | Asp | Phe | Arg | Ile | Tyr 575 | Gly | Leu | Ser | Thr | Lys 580 | Arg |
| Ile | Ala | Cys | Leu 585 | Leu | Glu | Lys | Lys | Thr 590 | Gly | Tyr | Ser | Gln | Glu 595 | Leu | Ala |
| Pro | Ser | Asp 600 | Asn | Pro | His | Val 605 | Leu | Val | Asp | Thr | Leu 610 | Thr | Ser | His | Ser |
| Phe | Thr 615 | Leu | Ser | Trp | Lys | Asp 620 | Tyr | Ser | Thr | Glu | Ser 625 | Gln | Pro | Gly | Phe |
| Ile 630 | Gln | Gly | Tyr | His | Val 635 | Tyr | Leu | Lys | Ser | Lys 640 | Ala | Arg | Gln | Cys | His 645 |
| Pro | Arg | Phe | Glu | Lys 650 | Ala | Val | Leu | Ser | Asp 655 | Gly | Ser | Glu | Cys | Cys 660 | Lys |
| Tyr | Lys | Ile | Asp 665 | Asn | Pro | Glu | Glu | Lys 670 | Ala | Leu | Ile | Val | Asp 675 | Asn | Leu |
| Lys | Pro | Glu 680 | Ser | Phe | Tyr | Glu | Phe 685 | Phe | Ile | Thr | Pro | Phe 690 | Thr | Ser | Ala |
| Gly | Glu 695 | Gly | Pro | Ser | Ala | Thr 700 | Phe | Thr | Lys | Val | Thr 705 | Thr | Pro | Asp | Glu |
| His 710 | Ser | Ser | Met | Leu | Ile 715 | His | Ile | Leu | Leu | Pro 720 | Met | Val | Phe | Cys | Val 725 |
| Leu | Leu | Ile | Met | Val 730 | Met | Cys | Tyr | Leu | Lys 735 | Ser | Gln | Trp | Ile | Lys 740 | Glu |
| Thr | Cys | Tyr | Pro 745 | Asp | Ile | Pro | Asp | Pro 750 | Tyr | Lys | Ser | Ser | Ile 755 | Leu | Ser |
| Leu | Ile | Lys 760 | Phe | Lys | Glu | Asn | Pro 765 | His | Leu | Ile | Ile | Met 770 | Asn | Val | Ser |
| Asp | Cys 775 | Ile | Pro | Asp | Ala | Ile 780 | Glu | Val | Val | Ser | Lys 785 | Pro | Glu | Gly | Thr |
| Lys 790 | Ile | Gln | Phe | Leu | Gly 795 | Thr | Arg | Lys | Ser | Leu 800 | Thr | Glu | Thr | Glu | Leu 805 |
| Thr | Lys | Pro | Asn | Tyr 810 | Leu | Tyr | Leu | Leu | Pro 815 | Thr | Glu | Lys | Asn | His 820 | Ser |
| Gly | Pro | Gly | Pro | Cys 825 | Ile | Cys | Phe | Glu | Asn 830 | Leu | Thr | Tyr | Asn | Gln 835 | Ala |
| Ala | Ser | Asp 840 | Ser | Gly | Ser | Cys | Gly 845 | His | Val | Pro | Val | Ser 850 | Pro | Lys | Ala |
| Pro | Ser 855 | Met | Leu | Gly | Leu | Met 860 | Thr | Ser | Pro | Glu | Asn 865 | Val | Leu | Lys | Ala |
| Leu 870 | Glu | Lys | Asn | Tyr | Met 875 | Asn | Ser | Leu | Gly | Glu 880 | Ile | Pro | Ala | Gly | Glu 885 |

-continued

```
Thr  Ser  Leu  Asn  Tyr  Val  Ser  Gln  Leu  Ala  Ser  Pro  Met  Phe  Gly  Asp
               890                      895                      900

Lys  Asp  Ser  Leu  Pro  Thr  Asn  Pro  Val  Glu  Ala  Pro  His  Cys  Ser  Glu
               905                      910                      915

Tyr  Lys  Met  Gln  Met  Ala  Val  Ser  Leu  Arg  Leu  Ala  Leu  Pro  Pro  Pro
               920                      925                      930

Thr  Glu  Asn  Ser  Ser  Leu  Ser  Ser  Ile  Thr  Leu  Leu  Asp  Pro  Gly  Glu
     935                      940                           945

His  Tyr  Cys
950
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i i ) IMMEDIATE SOURCE:
        ( B ) CLONE: FLAG peptide ( x i ) SEQUENCE DESCRIPTION: SEQ ID NO:7:

```
Asp  Tyr  Lys  Asp  Asp  Asp  Asp  Lys
 1                   5
```

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i i ) IMMEDIATE SOURCE:
        ( B ) CLONE: spacer peptide ( x i ) SEQUENCE DESCRIPTION: SEQ ID NO:8:

```
Asn  Arg  Tyr  Val
 1
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

```
Phe  Arg  Xaa  Arg  Cys
```

( 2 ) INFORMATION FOR SEQ ID NO:10:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Leu  Gln  Ile  Arg  Cys
   1                   5

( 2 ) INFORMATION FOR SEQ ID NO:11:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Trp  Ser  Xaa  Trp  Ser
   1                   5

RECEPTOR FOR ONCOSTATIN M

CROSS-REFERENCE TO RELATED APPLICATIONS

This application is a continuation-in-part of application Ser. No. 08/249,553, filed May 26, 1994, now abandoned.

BACKGROUND OF THE INVENTION

Oncostatin M is a secreted single-chain polypeptide cytokine that regulates the growth of certain tumor-derived and normal cell lines. A number of cell types have been found to bind the oncostatin M protein. See, for example, Linsley et al., *J. Biol. Chem.*, 264: 4282 (1989). Oncostatin M has been shown to inhibit proliferation of a number of tumor cell types (Linsley et al. supra). In contrast, however, this protein has been implicated in stimulating proliferation of Kaposi's sarcoma cells (Nair et al., *Science* 255:1430, 1992; Miles et al., *Science* 255:1432, 1992; and Cai et al., *Am. J. Pathol.* 145:74, 1994).

Identifying and isolating oncostatin M-binding proteins, such as cell surface oncostatin M receptors, is desirable for such reasons as enabling study of the biological signal transduced via the receptor. Such receptors in soluble form also could be used to competitively inhibit a biological activity of oncostatin M in various in vitro assays or in vivo procedures. A soluble form of the receptor could be administered to bind oncostatin M in vivo, thus inhibiting the binding of oncostatin M to endogenous cell surface receptors, for example.

A protein known as gp130 has been found to bind oncostatin M, but with relatively low affinity (Gearing et al., *Science* 255:1434, 1992). Heterodimeric receptors comprising a leukemia inhibitory factor (LIF) receptor and gp130 bind oncostatin M with higher affinity than does gp130 alone, but also bind LIF with high affinity (Gearing et al., supra). For certain applications, a receptor that binds oncostatin M with high affinity, but that does not function as a high affinity LIF receptor, would be advantageous. Prior to the present invention, no such receptor had been identified or isolated.

SUMMARY OF THE INVENTION

The present invention provides a novel polypeptide that is designated herein as the oncostatin M receptor β subunit (OSM-Rβ). Also provided is a receptor comprising OSM-Rβ linked (preferably covalently) to an oncostatin M-binding protein known as gp130. The gp130 polypeptide may be covalently linked to the OSM-Rβ polypeptide by any suitable means, such as via a cross-linking reagent or a polypeptide linker. In one embodiment of the invention, the receptor is a fusion protein produced by recombinant DNA technology. This receptor comprising OSM-Rβ and gp130 binds oncostatin M at levels greater than does gp130 alone. Disorders mediated by oncostatin M may be treated by administering a therapeutically effective amount of this inventive receptor to a patient afflicted with such a disorder.

DETAILED DESCRIPTION OF THE INVENTION

Figure 1:
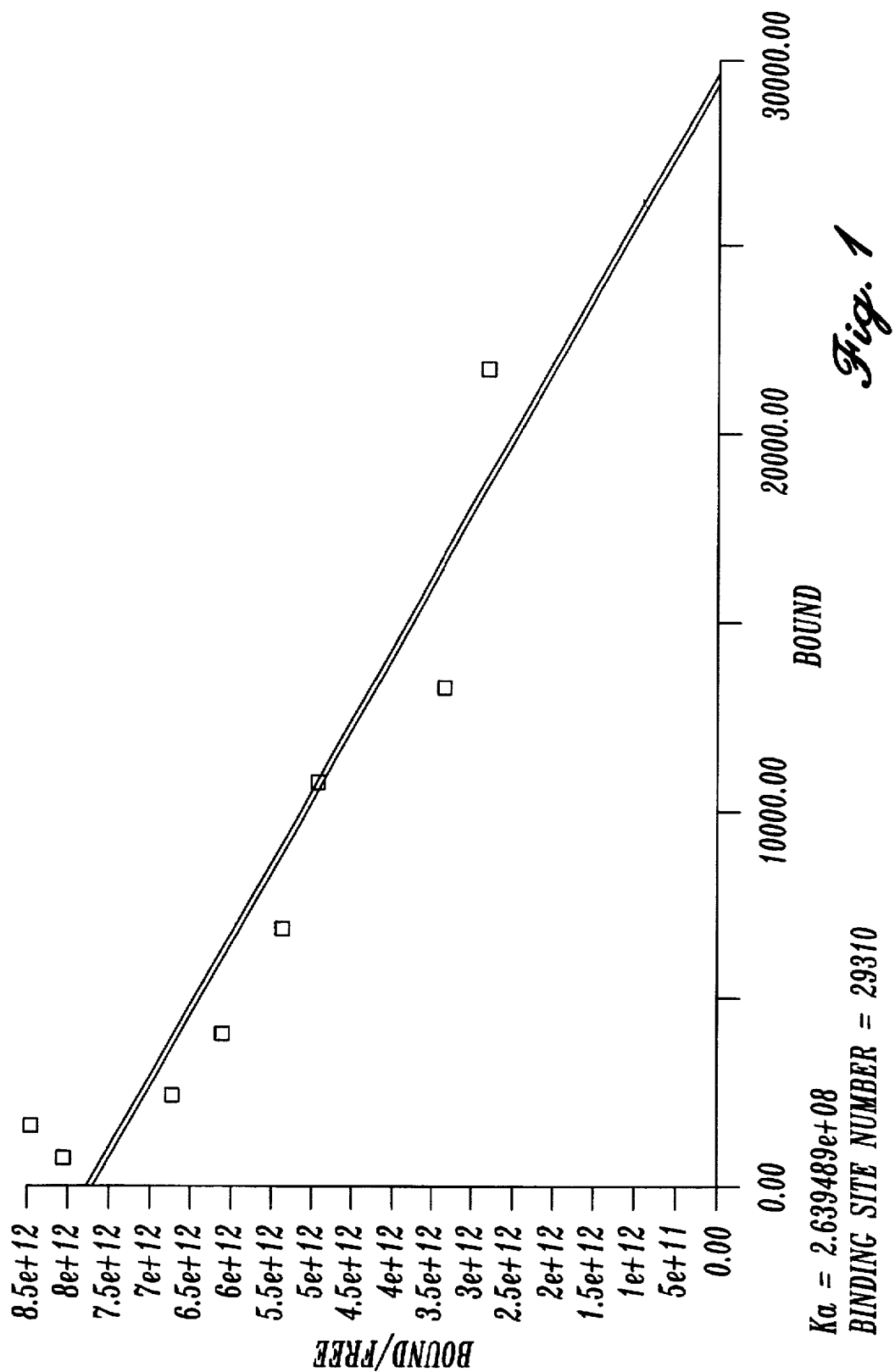
FIG. 1 presents a Scatchard analysis generated from an assay for binding of radioiodinated oncostatin M by cells expressing recombinant gp130. The assay is described in example 2.

The present invention provides a novel polypeptide designated the oncostatin M receptor β subunit (OSM-Rβ). Isolated DNA encoding OSM-Rβ, expression vectors containing OSM-Rβ DNA, and host cells transformed with such expression vectors are disclosed. Methods for production of recombinant OSM-Rβ polypeptides, including soluble forms of the protein, are also disclosed. Antibodies immunoreactive with the novel polypeptide are provided herein as well.

Another embodiment of the invention is directed to a receptor capable of binding oncostatin M, wherein the receptor comprises OSM-Rβ and gp130. The receptor finds use in various in vitro and in vivo procedures, including treatment of disorders mediated by oncostatin M.

DNA and encoded amino acid sequences of the OSM-Rβ cDNA isolated in example 1 are presented in SEQ ID NO:5 and SEQ ID NO:6. The encoded protein comprises (from N- to C-terminus) a signal peptide (amino acids −27 to −1 of SEQ ID NO:6) followed by an extracellular domain (amino acids 1 to 714), a transmembrane region (amino acids 715 to 734) and a cytoplasmic domain (amino acids 735 to 952). *E. coli* cells transformed with a recombinant vector comprising OSM-Rβ cDNA in the cloning vector pBluescript® SK- were deposited with the American Type Culture Collection, Rockville, Md., U.S.A., on Aug. 16, 1994, and assigned accession no. ATCC 69675.

The binding assay described in example 2 compared the binding of oncostatin M by cells expressing either gp130 alone or both gp130 and OSM-Rβ. The cells expressing both gp130 and OSM-Rβ exhibited higher affinity oncostatin M binding than did cells expressing gp130 alone. The assay described in example 5 demonstrates that OSM-Rβ alone does not bind oncostatin M at a detectable level. However, proteins expressed by cells co-transfected with both a soluble OSM-Rβ/Fc fusion protein-encoding vector and a soluble gp130/Fc fusion protein-encoding vector bound oncostatin M at higher levels than did proteins expressed by cells transfected with a soluble gp130/Fc-encoding vector alone.

In one embodiment, a receptor of the present invention comprises gp130 covalently linked to OSM-Rβ by any suitable means, such as via a cross-linking reagent or a polypeptide linker. The gp130 and OSM-Rβ proteins are covalently linked in a manner that does not interfere with the resulting receptor's ability to bind oncostatin M. In one embodiment, the receptor is a fusion protein produced by recombinant DNA technology.

Alternatively, the receptor may comprise gp130 non-covalently complexed with OSM-Rβ. Non-covalent bonding of gp130 to OSM-Rβ may be achieved by any suitable means that does not interfere with the receptor's ability to bind oncostatin M. In one approach, a first compound is attached to OSM-Rβ and a second compound that will non-covalently bond to the first compound is attached to gp130. Examples of such compounds are biotin and avidin. The receptor is thus formed through the non-covalent interactions of biotin with avidin. In one embodiment of the invention, OSM-Rβ and gp130 are recombinant polypeptides, each purified from recombinant cells and then non-covalently bonded together to form the receptor. A host cell may be transformed with two different expression vectors such that both OSM-Rβ and gp130 are produced by the recombinant host cell. OSM-Rβ and gp130 produced by such transformed host cells may associate to form a complex through non-covalent interactions. When such transformed cells express the membrane-bound forms of the proteins, such cells are useful in various assays, including competition assays.

The protein designated gp130 herein has been purified from cellular sources that include placental tissue and a myeloma cell line U266. A number of additional cell types have been found to express gp130 mRNA, as reported by Hibi et al., in Cell 63:1149 (1990). gp130 has been reported to be involved in the formation of high affinity interleukin-6 binding sites and in IL-6 signal transduction (Hibi et al. supra). gp130 also serves as an affinity converter for the LIF receptor (Gearing et al., Science 255:1434, 1992). The cloning and expression of cDNA encoding a full length gp130 protein has been reported by Hibi et al., supra, which is hereby incorporated by reference in its entirety.

As used herein, the terms OSM-Rβ and gp130 include variants and truncated forms of the native proteins that possess the desired biological activity. Variants produced by adding, substituting, or deleting amino acid(s) in the native sequence are discussed in more detail below.

One example of an OSM-Rβ polypeptide is that encoded by the cDNA clone described in example 1 (i.e., encoded by the OSM-Rβ cDNA insert of the recombinant vector in deposited strain ATCC 69675). Other OSM-Rβ polypeptides include those lacking all or part of the transmembrane region or the cytoplasmic domain of the protein. Additional truncated OSM-Rβ polypeptides may be chosen with regard to sequences that are conserved in the hematopoietin receptor family. The desirability of including the signal sequence depends on such factors as the position of the OSM-Rβ in a fusion protein and the intended host cells when the receptor is to be produced via recombinant DNA technology.

One example of a suitable gp130 polypeptide is that comprising the amino acid sequence presented in SEQ ID NO:2. E. coli strain DH5α cells transformed with a gp130-encoding recombinant vector designated B10G/pDC303 were deposited with the American Type Culture Collection, Rockville, Md., on Nov. 14, 1991, and assigned ATCC accession number 68827. The mammalian expression vector pDC303 (into which the gp130 cDNA has been inserted to form B10G/pDC303) is also known as SF CAV, and has been described in PCT application WO 93/19777. The nucleotide sequence of the gp130 cDNA contained in plasmid B10G/pDC303 and the amino acid sequence encoded thereby are presented in SEQ ID NO:1 and SEQ ID NO:2. The protein comprises (in order from the N-terminus to the C-terminus) a 22-amino acid signal sequence, complete extracellular domain (amino acids 1–597), a transmembrane region (beginning with amino acid 598), and a partial cytoplasmic domain (amino acids 621–686).

Alternatively, the gp130 protein disclosed by Hibi et al. supra may be employed. The eighth amino acid of the signal peptide is valine in the sequence reported by Hibi et al., but is leucine in SEQ ID NO:2 (at position −15). This difference in amino acid sequence may be attributable to genetic polymorphism (allelic variation among individuals producing the protein). In addition, the gp130 protein of SEQ ID NO:2 is truncated within the cytoplasmic domain, terminating with the leucine residue found at position 708 in the sequence presented in Hibi et al. supra. Although truncated, the gp130 protein of SEQ ID NO:2 comprises the extracellular domain responsible for oncostatin M binding, and thus is suitable for use as a component of the receptors of the present invention.

Regions of the gp130 protein corresponding to domains that are conserved among certain receptors are discussed by Hibi et al. supra, at page 1150, column 2, and page 1151, column 1. Other truncated gp130 polypeptides chosen to include these conserved regions may be employed.

Soluble OSM-Rβ and gp130 polypeptides are preferred for certain applications. In one embodiment of the present invention, the receptor comprises soluble OSM-Rβ covalently attached to soluble gp130. "Soluble OSM-Rβ" as used in the context of the present invention refers to polypeptides that are substantially similar in amino acid sequence to all or part of the extracellular region of a native OSM-Rβ and that, due to the lack of a transmembrane region that would cause retention of the polypeptide on a cell membrane, are secreted upon expression. Suitable soluble OSM-Rβ polypeptides retain the desired biological activity. Soluble OSM-Rβ may also include part of the transmembrane region or part of the cytoplasmic domain or other sequences, provided that the soluble OSM-Rβ protein is capable of being secreted.

Likewise, the term "soluble gp130" as used herein refers to proteins that are substantially similar in amino acid sequence to all or part of the extracellular region of a native gp130 and are secreted upon expression but retain the desired biological activity. Soluble gp130 may include part of the transmembrane region, cytoplasmic domain, or other sequences, as long as the polypeptide is secreted.

In one embodiment, soluble OSM-Rβ and gp130 polypeptides include the entire extracellular domain. To effect secretion, the soluble polypeptides comprise the native signal peptide or a heterologous signal peptide. Thus, examples of soluble OSM-Rβ polypeptides comprise amino acids −27 to 714 or 1 to 714 of SEQ ID NO:6. Examples of soluble gp130 polypeptides comprise amino acids −22 to 597 or 1 to 597 of SEQ ID NO:2.

Additional examples of soluble gp130 polypeptides are those lacking from one to all three of the fibronectin domains found within the extracellular domain, as described in example 4 below. These soluble gp130 polypeptides include those comprising amino acids −22 to y or 1 to y of SEQ ID NO:2, wherein y is an integer between 308 and 597, inclusive.

A soluble fusion protein comprising amino acids −27 through 432 of the OSM-Rβ of SEQ ID NO:6 fused to an antibody Fc region polypeptide is described in example 5. The OSM-Rβ moiety of the fusion protein, which is a fragment of the OSM-Rβ extracellular domain, retained the desired biological activity. Thus, examples of soluble OSM-Rβ polypeptides comprise amino acids −27 to x, or 1 to x of SEQ ID NO:6, wherein x is an integer between 432 and 714, inclusive.

Soluble OSM-Rβ and soluble gp130 may be identified (and distinguished from their non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of OSM-Rβ or gp130 in the medium indicates that the protein was secreted from the cells and thus is a soluble form of the desired protein. Soluble OSM-Rβ and soluble gp130 may be naturally-occurring forms of these proteins. Alternatively, soluble fragments of OSM-Rβ and gp130 proteins may be produced by recombinant DNA technology or otherwise isolated, as described below.

The use of soluble forms of OSM-Rβ and gp130 is advantageous for certain applications. Purification of the proteins from recombinant host cells is facilitated, since the soluble proteins are secreted from the cells. Further, a receptor of the present invention comprising soluble OSM-Rβ and gp130 proteins is generally more suitable for intravenous administration.

With respect to the foregoing discussion of signal peptides and the various domains of the gp130 and OSM-Rβ proteins, the skilled artisan will recognize that the above-described boundaries of such regions of the proteins are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, the OSM-Rβ transmembrane region was identified by computer program prediction in combination with homology to the transmembrane region of the LIF receptor protein described by Gearing et al. (*EMBO J.* 10:2839, 1991). Thus, soluble OSM-Rβ polypeptides comprising the extracellular domain include those having a C-terminal amino acid that may vary from that identified above as the C-terminus of the extracellular domain. Further, post-translational processing that can vary according to the particular expression system employed may yield proteins having differing N-termini. Such variants that retain the desired biological activities are encompassed by the terms "OSM-Rβ polypeptides" and "gp130 polypeptides" as used herein.

Truncated OSM-Rβ and gp130, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. Oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The well known polymerase chain reaction procedure also may be employed to isolate a DNA sequence encoding a desired protein fragment. Oligonucleotide primers comprising the desired termini of the fragment are employed in such a polymerase chain reaction. Any suitable PCR procedure may be employed. One such procedure is described in Saiki et al., *Science* 239:487 (1988). Another is described in *Recombinant DNA Methodology*, Wu et al., eds., Academic Press Inc., San Diego (1989), pp. 189–196. In general, PCR reactions involve combining the 5' and 3' oligonucleotide primers with template DNA (in this case, OSM-Rβ or gp130 DNA) and each of the four deoxynucleoside triphosphates, in a suitable buffered solution. The solution is heated, (e.g. from 95° to 100° C.) to denature the double-stranded DNA template and is then cooled before addition of a DNA polymerase enzyme. Multiple cycles of the reactions are carried out in order to amplify the desired DNA fragment.

The gp130 polypeptide is attached to the OSM-Rβ polypeptide through a covalent or non-covalent linkage. Covalent attachment is preferred for certain applications. e.g. in vivo use, in view of the enhanced stability generally conferred by covalent, as opposed to non-covalent, bonds. In constructing the receptor of the present invention, covalent linkage may be accomplished via cross-linking reagents, peptide linkers, or any other suitable technique.

Numerous reagents useful for cross-linking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains, thus linking one polypeptide to another.

One type of peptide linker that may be employed in the present invention separates gp130 and OSM-Rβ domains by a distance sufficient to ensure that each domain properly folds into the secondary and tertiary structures necessary for the desired biological activity. The linker also should allow the extracellular domains of gp130 and OSM-Rβ to assume the proper spatial orientation to form the binding site for oncostatin M.

Suitable peptide linkers are known in the art, and may be employed according to conventional techniques. Among the suitable peptide linkers are those described in U.S. Pat. Nos. 4,751,180 and 4,935,233, which are hereby incorporated by reference. A peptide linker may be attached to gp130 and to OSM-Rβ by any of the conventional procedures used to attach one polypeptide to another. The cross-linking reagents available from Pierce Chemical Company as described above are among those that may be employed. Amino acids having side chains reactive with such reagents may be included in the peptide linker, e.g., at the termini thereof. Preferably, a fusion protein comprising gp130 joined to OSM-Rβ via a peptide linker is prepared by recombinant DNA technology.

In one embodiment of the invention, OSM-Rβ and gp130 are linked via polypeptides derived from immunoglobulins. Preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). As one example, a polypeptide derived from the Fc region of an antibody may be attached to the C-terminus of OSM-Rβ. A separate Fc polypeptide is attached to the C-terminus of gp130. Disulfide bonds form between the two Fc polypeptides (e.g., in the so-called hinge region, where interchain disulfide bonds are normally present in antibody molecules), producing a heterodimer comprising the gp130 and to OSM-Rβ/Fc fusion protein linked to the gp130/Fc fusion protein. Advantageously, host cells are co-transfected with two different expression vectors, one encoding soluble OSM-Rβ/Fc and the other encoding soluble gp130/Fc. The heterodimer is believed to form intracellularly or during secretion.

The term "Fc polypeptide" as used herein includes native and mutein forms, as well as truncated Fc polypeptides containing the hinge region that promotes dimerization.

cDNA encoding a single chain polypeptide derived from the Fc region of a human IgG1 antibody has been cloned into the pBluescript SK® cloning vector (Stratagene Cloning Systems, LaJolla, Calif.) to produce a recombinant vector designated hIgG1Fc. A unique BglII site is positioned near the 5' end of the inserted Fc encoding sequence. An SpeI site is immediately downstream of the stop codon. The DNA and encoded amino acid sequences of the cloned Fc cDNA are presented in SEQ ID NO:3 and SEQ ID NO:4. The Fc polypeptide encoded by the cDNA extends from the N-terminal hinge region to the native C-terminus, i.e., is an essentially full-length antibody Fc region. One suitable mutein of this Fc polypeptide is described in U.S. patent application Ser. No. 08/097,827, hereby incorporated by reference. The mutein exhibits reduced affinity for Fc receptors.

Homodimers comprising two OSM-Rβ/Fc polypeptides or two gp130/Fc polypeptides linked via disulfide bonds are also produced by certain of the transfected host cells disclosed herein. The homodimers may be separated from each other and from the heterodimer by virtue of differences in size (e.g., by gel electrophoresis). The heterodimer also may be purified by sequential immunoaffinity chromatography (described below).

In an alternative embodiment, a first fusion polypeptide comprising gp130 (or a fragment thereof) upstream of the constant region of an antibody light chain (or a fragment thereof) is prepared. A second fusion polypeptide comprises OSM-Rβ upstream of the constant region of an antibody heavy chain (or a heavy chain fragment, the N-terminus of which extends at least through the $C_H 1$ region. Disulfide bond(s) form between the gp130-light chain fusion polypeptide and the OSM-Rβ-heavy chain fusion polypeptide, thus producing a receptor of the present invention. As a further alternative, an OSM-Rβ-antibody light chain fusion polypeptide is prepared and combined with (disulfide bonded to) a fusion polypeptide comprising gp130 fused to an antibody heavy chain. When two of the foregoing disulfide bonded molecules are combined, additional disulfide bonds form between the two Fc regions. The resulting receptor of the present invention comprising four fusion polypeptides resembles an antibody in structure and displays the oncostatin M binding site bivalently.

The gp130 and OSM-Rβ polypeptides may be separately purified from cellular sources, and then linked together. Alternatively, the receptor of the present invention may be produced using recombinant DNA technology. The gp130 and OSM-Rβ polypeptides may be produced separately and purified from transformed host cells for subsequent covalent linkage. In one embodiment of the present invention, a host cell is transformed/transfected with foreign DNA that encodes gp130 and OSM-Rβ as separate polypeptides. The two polypeptides may be encoded by the same expression vector with start and stop codons for each of the two genes, or the recombinant cells may be co-transfected with two separate expression vectors. In another embodiment, the receptor is produced as a fusion protein in recombinant cells.

In one embodiment of the present invention, the receptor protein is a recombinant fusion protein of the formula:

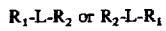

wherein $R_1$ represents gp130 or a gp130 fragment; $R_2$ represents OSM-Rβ or an OSM-Rβ fragment; and L represents a peptide linker.

The fusion proteins of the present invention include constructs in which the C-terminal portion of gp130 is fused to the linker which is fused to the N-terminal portion of OSM-Rβ, and also constructs in which the C-terminal portion of OSM-Rβ is fused to the linker which is fused to the N-terminal portion of gp130. gp130 is covalently linked to OSM-Rβ in such a manner as to produce a single protein which retains the desired biological activities of gp130 and OSM-Rβ. The components of the fusion protein are listed in their order of occurrence (i.e., the N-terminal polypeptide is listed first, followed by the linker and then the C-terminal polypeptide).

A DNA sequence encoding a fusion protein is constructed using recombinant DNA techniques to insert separate DNA fragments encoding gp130 and OSM-Rβ into an appropriate expression vector. The 3' end of a DNA fragment encoding gp130 is ligated (via the linker) to the 5' end of the DNA fragment encoding OSM-Rβ with the reading frames of the sequences in phase to permit translation of the mRNA into a single biologically active fusion protein. Alternatively, the 3' end of a DNA fragment encoding OSM-Rβ may be ligated (via the linker) to the 5' end of the DNA fragment encoding gp130, with the reading frames of the sequences in phase to permit translation of the mRNA into a single biologically active fusion protein. A DNA sequence encoding an N-terminal signal sequence may be retained on the DNA sequence encoding the N-terminal polypeptide, while stop codons, which would prevent read-through to the second (C-terminal) DNA sequence, are eliminated. Conversely, a stop codon required to end translation is retained on the second DNA sequence. DNA encoding a signal sequence is preferably removed from the DNA sequence encoding the C-terminal polypeptide.

A DNA sequence encoding a desired polypeptide linker may be inserted between, and in the same reading frame as, the DNA sequences encoding gp130 and OSM-Rβ using any suitable conventional technique. For example, a chemically synthesized oligonucleotide encoding the linker and containing appropriate restriction endonuclease cleavage sites may be ligated between the sequences encoding gp130 and OSM-Rβ.

Alternatively, a chemically synthesized DNA sequence may contain a sequence complementary to the 3' terminus (without the stop codon) of either gp130 or OSM-Rβ, followed by a linker-encoding sequence which is followed by a sequence complementary to the 5' terminus of the other of gp130 and OSM-Rβ. Oligonucleotide directed mutagenesis is then employed to insert the linker-encoding sequence into a vector containing a direct fusion of gp130 and OSM-Rβ.

The present invention provides isolated DNA sequences encoding the above-described fusion proteins comprising gp130, OSM-Rβ, and a peptide linker. DNA encoding the novel OSM-Rβ polypeptides disclosed herein is also provided, as is DNA encoding OSM-Rβ polypeptides fused to immunoglobin-derived polypeptides. OSM-Rβ-encoding DNA encompassed by the present invention includes, for example, cDNA, chemically synthesized DNA, DNA isolated by PCR, genomic DNA, and combinations thereof. Genomic OSM-Rβ DNA may be isolated using the cDNA isolated in Example 1, or fragments thereof, as a probe using standard techniques.

Also provided herein are recombinant expression vectors containing the isolated DNA sequences. "Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein which is transcribed into mRNA and translated into protein, and (3) appropriate transcription and translation initiation and termination sequences. The choice of promoter and other regulatory elements generally varies according to the intended host cell.

In the expression vectors, regulatory elements controlling transcription or translation are generally derived from mammalian, microbial, viral or insect genes. The ability to replicate in a host, usually conferred by an origin of replication, and a selection gene to facilitate recognition of transformants may additionally be incorporated. Vectors derived from retroviruses also may be employed.

DNA regions are operably linked when they are functionally related to each other. For example, DNA encoding a signal peptide (secretory leader) is operably linked to DNA for a polypeptide if the polypeptide is expressed as a precursor that is secreted through the host cell membrane; a promoter is operably linked to a coding sequence if it controls the transcription of the sequence; and a ribosome binding site is operably linked to a coding sequence if it is positioned so as to permit translation. Generally, "operably linked" means contiguous and, in the case of secretory leaders, contiguous and in reading frame.

Transformed host cells are cells which have been transformed or transfected with foreign DNA using recombinant DNA techniques. In the context of the present invention, the foreign DNA includes a sequence encoding the inventive proteins. Host cells may be transformed for purposes of cloning or amplifying the foreign DNA, or may be transformed with an expression vector for production of the protein. Suitable host cells include prokaryotes, yeast or higher eukaryotic cells. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotes include gram negative or gram positive organisms, for example *E. coli* or bacilli. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and this provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermoinducible repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

The recombinant receptor protein may also be expressed in yeast hosts, preferably from Saccharomyces species, such as *S. cerevisiae*. Yeast of other genera such as Pichia or Kluyveromyces may also be employed. Yeast vectors will generally contain an origin of replication from the 2 μm yeast plasmid or an autonomously replicating sequence (ARS), a promoter, DNA encoding the receptor fusion protein, sequences for polyadenylation and transcription termination and a selection gene. Preferably, yeast vectors will include an origin of replication and selectable markers permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al., (*Nature* 300:724, 1982). The yeast (α-factor leader, which directs secretion of heterologous proteins, can be inserted between the promoter and the structural gene to be expressed. See, e.g., Kurjan et al., *Cell* 30:922, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al., *Proc. Natl. Acad. Sci. USA* 75:1929, (1978), selecting for Trp$^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include L cells, C127, 3T3, Chinese hamster ovary (CHO), HeLa, and BHK cell lines. Additional suitable mammalian host cells include CV-1 cells (ATCC CCL70) and COS-7 cells (ATCC CRL 1651; described by Gluzman, *Cell* 23:175, 1981), both derived from monkey kidney. Another monkey kidney cell line, CV-1/EBNA (ATCC CRL 10478), was derived by transfection of the CV-1 cell line with a gene encoding Epstein-Barr virus nuclear antigen-1 (EBNA-1) and with a vector containing CMV regulatory sequences (McMahan et al., *EMBO J.* 10:2821, 1991). The EBNA-1 gene allows for episomal replication of expression vectors, such as HAV-EO or pDC406, that contain the EBV origin of replication.

Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and poly-adenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included.

Exemplary vectors can be constructed as disclosed by Okayama and Berg (*Mol. Cell. Biol.* 3:280, 1983). One useful system for stable high level expression of mammalian receptor cDNAs in C127 murine mammary epithelial cells can be constructed substantially as described by Cosman et al. (*Mol. Immunol.* 23:935, 1986). Vectors derived from retroviruses also may be employed.

When secretion of the OSM-Rβ protein from the host cell is desired, the expression vector may comprise DNA encoding a signal or leader peptide. In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460, 846.

The present invention provides a process for preparing the recombinant proteins of the present invention, comprising culturing a host cell transformed with an expression vector comprising a DNA sequence that encodes said protein under conditions that promote expression. The desired protein is then purified from culture media or cell extracts. The desired protein may be OSM-Rβ or the heterodimeric receptor, for example. Cell-free translation systems could also be employed to produce the desired protein using RNA derived from the novel DNA of the present invention.

As one example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise oncostatin M. An oncostatin M affinity matrix may be prepared by coupling recombinant human oncostatin M to cyanogen bromide-activated Sepharose (Pharmacia) or Hydrazide Affigel (Biorad), according to manufacturer's recommendations. Sequential immunopurification using antibodies bound to a suitable support is preferred. Proteins binding to an antibody specific for OSM-Rβ are recovered and contacted with antibody specific for gp130 on an insoluble support. Proteins immunoreactive with both antibodies may thus be identified and isolated.

Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify a fusion protein.

Some or all of the foregoing purification steps, in various combinations, can be employed to provide an essentially homogeneous recombinant protein. Recombinant cell culture enables the production of the fusion protein free of those contaminating proteins which may be normally associated with gp130 or OSM-Rβ as they are found in nature in their respective species of origin, e.g., on the surface of certain cell types.

The foregoing purification procedures are among those that may be employed to purify non-recombinant receptors of the present invention as well. When linking procedures that may produce homodimers (gp130-linker-gp130 and OSM-Rβ-linker-OSM-Rβ) are employed, purification procedures that separate the heterodimer from such homodimers are employed. An example of such a procedure is sequential immunopurification as discussed above. In one embodiment, OSM-Rβ (recombinant or non-recombinant) is purified such that no bands corresponding to other (contaminating) proteins are detectable by SDS-PAGE.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984), involving two sequential, reversed-phase HPLC steps for purification of a recombinant protein on a preparative HPLC column.

The DNA or amino acid sequences of gp130 and OSM-Rβ may vary from those presented in SEQ ID NO:1 and SEQ ID NO:5, respectively. Due to the known degeneracy of the genetic code, there can be considerable variation in nucleotide sequences encoding the same amino acid sequence. In addition, DNA sequences capable of hybridizing to the native DNA sequence of SEQ ID NO:1 or SEQ ID NO:5 under moderately stringent or highly stringent conditions, and which encode a biologically active gp130 or OSM-Rβ polypeptide, respectively, are also considered to be gp130-encoding or OSM-Rβ-encoding DNA sequences, in the context of the present invention. Such hybridizing sequences include but are not limited to variant sequences such as those described below, and DNA derived from other mammalian species. Human OSM-Rβ is within the scope of the present invention, as are OSM-Rβ proteins derived from other mammalian species, including but not limited to rat, bovine, porcine, or various non-human primates.

Moderately stingent conditions include conditions described in, for example, Sambrook et al, *Molecular Cloning: A Laboratory Manual*, 2nd ed., Vol. 1, pp 1.101–1.04, Cold Spring Harbor Laboratory Press, 1989. Conditions of moderate stingency, as defined by Sambrook et al., include use of a prewashing solution of 5× SSC, 0.5% SDS, 1.0 mM EDTA (pH 8.0) and hybridization conditions of about 55° C., 5× SSC, overnight. Highly stringent conditions include higher temperatures of hybridization and washing. The skilled artisan will recognize that the temperature and wash solution salt concentration may be adjusted as necessary according to factors such as the length of the probe. One embodiment of the invention is directed to DNA sequences that will hybridize to the OSM-Rβ DNA of SEQ ID NO:5 under highly stringent conditions, wherein said conditions include hybridization at 68° C. followed by washing in 0.1× SSC/0.1% SDS at 63°–68° C. In another embodiment, the present invention provides a heterodimeric receptor comprising OSM-Rβ and gp130, wherein said OSM-Rβ and gp130 are encoded by DNA that hybridizes to the DNA of SEQ ID NO:5 or SEQ ID NO:1, respectively, under moderately or highly stringent conditions.

Further, certain mutations in a nucleotide sequence which encodes OSM-Rβ or gp130 will not be expressed in the final protein product. For example, nucleotide substitutions may be made to enhance expression, primarily to avoid secondary structure loops in the transcribed mRNA (see EP 75,444A). Other alterations of the nucleotide sequence may be made to provide codons that are more readily translated by the selected host, e.g., the well-known *E. coli* preference codons for *E. coli* expression.

The amino acid sequence of native gp130 or OSM-Rβ may be varied by substituting, deleting, adding, or inserting one or more amino acids to produce a gp130 or OSM-Rβ variant. Variants that possess the desired biological activity of the native gp130 and OSM-Rβ proteins may be employed in the receptor of the present invention. Assays by which the biological activity of variant proteins may be analyzed are described in the examples below. Biologically active gp130 polypeptides are capable of binding oncostatin M. The desired biological activity of the OSM-Rβ polypeptides disclosed herein is the ability to enhance the binding of oncostatin M when OSM-Rβ is joined to gp130, compared to the level of oncostatin M binding to gp130 alone.

Alterations to the native amino acid sequence may be accomplished by any of a number of known techniques. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craig (*BioTechniques*, January 1985, 12–19); Smith et al. (*Genetic Engineering: Principles and Methods*, Plenum Press, 1981); U.S. Pat. No. 4,518,584, and U.S. Pat. No. 4,737,462, which are incorporated by reference herein.

Bioequivalent variants of OSM-Rβ and gp130 may be constructed by, for example, making various substitutions of amino acid residues or deleting terminal or internal amino acids not needed for biological activity. In one embodiment of the invention, the variant amino acid sequence is at least 80% identical, preferably at least 90% identical, to the native sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv, Appl. Math. 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequecnce and Structure*, National Biomedical Research Foundation, pp. 353–358, 1979; (2) a penalty of 3.0 for each gap and an additional 0.10 penalty for each symbol in each gap; and (3) no penalty for end gaps.

Generally, substitutions should be made conservatively; i.e., the most preferred substitute amino acids are those having physiochemical characteristics resembling those of the residue to be replaced. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Cysteine residues can be deleted or replaced with other amino acids to prevent formation of unnecessary or incorrect intramolecular disulfide bridges upon renaturation. Hydrophilic amino acids may be substituted for hydrophobic amino acids in the transmembrane region and/or intracellular domain of gp130 and OSM-Rβ to enhance water solubility of the proteins.

Adjacent dibasic amino acid residues may be modified to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg—Arg, Arg-Lys, and Lys-Arg pairs to eliminate the occurrence of these adjacent basic residues. These amino acid pairs, which constitute KEX2 proteases processing sites, are found at residues 290–291, 291–292, 580–581, and 797–798 of the OSM-Rβ protein of SEQ ID NO:6. These KEX2 sites are found at positions 153–154 and 621–622 of the gp130 protein of SEQ ID NO:2. Lys—Lys pairings are considerably less susceptible to KEX2 cleavage, and conversion of Arg-Lys or Lys-Arg to Lys—Lys represents a conservative and preferred approach to inactivating KEX2 sites.

The present invention also includes proteins with or without associated native-pattern glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where A1 is any amino acid except Pro, and Z is Ser or Thr. In this sequence, asparagine provides a side chain amino group for covalent attachment of carbohydrate.

The OSM-Rβ amino acid sequence in SEQ ID NO:6 contains 16 such N-glycosylation sites, all found in the extracellular domain, at amino acids 15–17, 57–59, 104–106, 136–138, 149–151, 194–196, 280–282, 299–301, 318–320, 334–336, 353–355, 395–397, 419–421, 464–466, 482–484, and 553–555 of SEQ ID NO:6. The extracellular domain of gp130 comprises N-glycosylation sites at positions 21–23, 61–63, 109–111, 135–137, 205–207, 224–226, 357–359, 361–363, 368–370, 531–533, and 542–544 of SEQ ID NO:2. Such a site can be eliminated by substituting another amino acid for Asn or for residue Z, deleting Asn or Z, or inserting a non-Z amino acid between $A_1$ and Z, or an amino acid other than Asn between Asn and $A_1$. Known procedures for inactivating N-glycosylation sites in proteins include those described in U.S. Pat. No. 5,071,972 and EP 276,846.

Variants of the receptor proteins of the present invention also include various structural forms of the primary protein which retain biological activity. Due to the presence of ionizable amino and carboxyl groups, for example, a receptor protein may be in the form of acidic or basic salts, or may be in neutral form. Individual amino acid residues may also be modified by oxidation or reduction.

The primary amino acid structure also may be modified by forming covalent or aggregative conjugates with other chemical moieties, such as glycosyl groups, lipids, phosphate, acetyl groups and the like. Covalent derivatives are prepared by linking particular functional groups to amino acid side chains or at the N- or C- termini. Other derivatives of the receptor protein within the scope of this invention include covalent or aggregative conjugates of the receptor protein with other proteins or polypeptides, such as by synthesis in recombinant culture as N- or C- terminal fusions. For example, the conjugated polypeptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Peptides may be fused to the desired protein (e.g., via recombinant DNA techniques) to facilitate purification or identification. Examples include poly-His or the Flag® peptide Asp-Tyr-Lys-Asp-Asp-Asp-Asp-Lys (SEQ ID NO:7) (Hopp et al., *BiolTechnology* 6:1204, 1988, and U.S. Pat. No. 5,011,912). The Flag® peptide is highly antigenic and provides an epitope reversibly bound by a specific monoclonal antibody, enabling rapid assay and facile purification of expressed recombinant protein. Expression systems useful for fusing the Flag® octapeptide to the N- or C-terminus of a given protein are available from Eastman Kodak Co., Scientific Imaging Systems Division, New Haven, Conn., as are monoclonal antibodies that bind the octapeptide.

Encompassed by the present invention are OSM-Rβ polypeptides in the form of oligomers, such as dimers or trimers. Such oligomers may be naturally occurring or produced by recombinant DNA technology. The present invention provides oligomers of OSM-Rβ (preferably the extracellular domain or a fragment thereof), linked by disulfide bonds or expressed as fusion proteins with or without peptide linkers. Oligomers may be formed by disulfide bonds between cysteine residues on different OSM-Rβ polypeptides, for example. In another embodiment, OSM-Rβ oligomers may be prepared using polypeptides derived from immunoglobulins, as described above.

Naturally occurring OSM-Rβ variants are also encompassed by the present invention. Examples of such variants are proteins that result from alternative mRNA splicing events or from proteolytic cleavage of the OSM-Rβ protein, wherein the desired biological activity is retained. Alternative splicing of mRNA may yield a truncated but biologically active OSM-Rβ protein, such as a naturally occurring soluble form of the protein, for example. Variations attributable to proteolysis include, for example, differences in the N- or C-termini upon expression in different types of host cells, due to proteolytic removal of one or more terminal amino acids from the OSM-Rβ protein (generally from 1–5 terminal amino acids). Naturally occurring gp130 variants may be employed in the inventive receptors.

The present invention also provides a pharmaceutical composition comprising a receptor protein of the present invention with a physiologically acceptable carrier or diluent. Such carriers and diluents will be nontoxic to recipients at the dosages and concentrations employed. Such compositions may, for example, comprise the receptor protein in a buffered solution, to which may be added antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients. The receptor of the present invention may be administered by any suitable method in a manner appropriate to the indication, such as intravenous injection, local administration, continuous infusion, sustained release from implants, etc.

The heterodimeric receptor of the present invention (comprising gp130 and OSM-Rβ) is useful as an oncostatin M binding reagent. This receptor, which preferably comprises soluble gp130 and soluble OSM-Rβ, has applications both in vitro and in vivo. The receptors may be employed in in vitro assays, e.g., in studies of the mechanism of transduction of the biological signal that is initiated by binding of oncostatin M to this receptor on a cell. Such receptors also could be used to inhibit a biological activity of oncostatin M in various in vitro assays or in vivo procedures. In one embodiment of the invention, the inventive receptor is administered to bind oncostatin M, thus inhibiting binding of the oncostatin M to endogenous cell surface receptors. Biological activity mediated by such binding of oncostatin M to the cells thus is also inhibited. gp130 alone binds oncostatin M, but with relatively low affinity (Gearing et al., *Science* 255:1434, 1992). Heterodimeric receptors comprising a leukemia inhibitory factor (LIF) receptor and gp130 bind oncostatin M with higher affinity than does gp130 alone, but also bind LIF with high affinity (Gearing et al., supra). Receptors of the present invention, produced by cells co-transfected with OSM-Rβ- and gp130-encoding DNA, for example, bind oncostatin M with high affinity but do not function as a high affinity LIF receptors. Such receptors of the present invention may be employed when inhibition of an oncostatin M-mediated activity, but not a LIF-mediated activity, is desired, for example. Oncostatin M shares certain properties with LIF, but exhibits other activities that are not exhibited by LIF. In addition, use of the receptors of the present invention in vitro assays offers the advantage of allowing one to determine that the assay results are attributable to binding of oncostain M, but not LIF, by the receptor.

In one embodiment of the invention, a heterodimeric receptor comprising OSM-Rβ and gp130 is administered in vivo to inhibit a biological activity of oncostatin M. Oncostatin M has exhibited growth modulating activity on a variety of different cell types, and has been reported to stimulate hematopoiesis, stimulate epithelial cell proliferation, increase plasmin activity (thereby inducing fibrinolysis), inhibit angiogenesis and supress expression of major histocompatibility complex antigens on endothelial cells. See PCT application WO 9109057 and European patent application no. 422,186. When these or other biological effects of oncostatin M are undesirable, a receptor of the present invention may be administered to bind oncostatin M.

The inventive receptor may be administered to a patient in a therapeutically effective amount to treat a disorder mediated by oncostatin M. A disorder is said to be mediated by oncostatin M when oncostatin M causes (directly or indirectly) or exacerbates the disorder. Soluble receptor proteins can be used to competitively bind to oncostatin M, thereby inhibiting binding of oncostatin M to endogenous cell surface receptors. Oncostatin M is believed to stimulate production of the cytokine interleukin-6 (IL-6), as reported by Brown et al., *J. Immunol.* 147:2175 (1991). Oncostatin M therefore may indirectly mediate disorders associated with the presence of IL-6. IL-6 has been reported to be involved in the pathogenesis of AIDS-associated Kaposi's sarcoma (deWit et al., *J. Intern. Med.* [*England*] 229:539, 1991). Oncostatin M has been reported to play a role in stimulating proliferation of Kaposi's sarcoma cells (Nair et al., *Science* 255:1430, 1992, and Miles et al., *Science* 255:1432, 1992). Binding of oncostatin M by a receptor of the present invention (preferably a soluble form thereof) thus may be useful in treating Kaposi's sarcoma.

Heterodimeric receptors comprising OSM-Rβ linked to gp130 also find use in assays for biological activity of oncostatin M proteins, which biological activity is measured in terms of binding affinity for the receptor. To illustrate, the receptor may be employed in a binding assay to measure the biological activity of an oncostatin M fragment, variant, or mutein. The receptor is useful for determining whether biological activity of oncostatin M is retained after modification of an oncostatin M protein (e.g., chemical modification, mutation, etc.). The binding affinity of the modified oncostatin M protein for the receptor is compared to that of an unmodified oncostatin M protein to detect any adverse impact of the modification on biological activity. Biological activity thus can be assessed before the modified protein is used in a research study or assay, for example.

The heterodimeric receptors also find use as reagents that may be employed by those conducting "quality assurance" studies, e.g., to monitor shelf life and stability of oncostatin M proteins under different conditions. The receptors may be used to confirm biological activity (in terms of binding affinity for the receptor) in oncostatin M proteins that have been stored at different temperatures, for different periods of time, or which have been produced in different types of recombinant expression systems, for example.

The present invention further provides fragments of the OSM-Rβ nucleotide sequences presented herein. Such fragments desirably comprise at least about 14 nucleotides of the sequence presented in SEQ ID NO:5. DNA and RNA complements of said fragments are provided herein, along with both single-stranded and double-stranded forms of the OSM-Rβ DNA.

Among the uses of such nucleic acid fragments is use as a probe. Such probes may be employed in cross-species hybridization procedures to isolate OSM-Rβ DNA from additional mammalian species. As one example, a probe corresponding to the extracellular domain of OSM-Rβ may be employed. The probes also find use in detecting the presence of OSM-Rβ nucleic acids in in vitro assays and in such procedures as Northern and Southern blots. Cell types expressing OSM-Rβ can be identified. Such procedures are well known, and the skilled artisan can choose a probe of suitable length, depending on the particular intended application. The probes may be labeled (e.g., with $^{32}P$) by conventional techniques.

Other useful fragments of the OSM-Rβ nucleic acids are antisense or sense oligonucleotides comprising a single-stranded nucleic acid sequence (either RNA or DNA) capable of binding to target OSM-Rβ mRNA (sense) or OSM-Rβ DNA (antisense) sequences. Antisense or sense oligonucleotides, according to the present invention, may comprise a fragment of the coding region of OSM-Rβ cDNA. Such a fragment generally comprises at least about 14 nucleotides, preferably from about 14 to about 30 nucleotides. The ability to create an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of OSM-Rβ proteins.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retroviral vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate certain embodiments of the invention, and are not to be construed as limiting the scope of the invention.

EXAMPLES

Example 1

Isolation of DNA Encoding OSM-Rβ

DNA encoding the β subunit of the oncostatin M receptor was isolated as follows. The procedure began with preparation of oligonucleotides degenerate to amino acid sequences that are conserved among proteins of the hematopoietin receptor family.

Alignment of the amino acid sequences of three proteins in the hematopoietin receptor family (gp130, LIF receptor, and G-CSF receptor) reveals several highly conserved regions. Such conserved regions are identified and discussed by Gearing et al. in *Polyfunctional Cytokines: IL-6 and LIF*, Bock et al., Eds., John Wiley & Sons, Chichester, UK, 1992, page 245. After including homologous sequences from the γ chain of the IL-2 receptor as well (Takeshita et al. *Science* 257:379, 1992), oligonucleotides degenerate to certain of the conserved regions (i.e., sets of oligonucleotides that include all possible DNA sequences that can encode the amino acid sequences in the conserved regions) were prepared by conventional techniques.

Two sets of degenerate oligonucleotides were used as primers in a polymerase chain reaction (PCR). 5' primers were degenerate to the amino acid sequence PheArgXArgCys (SEQ ID NO:9), which is found at positions 275–279 of the gp130 sequence of SEQ ID NO:2, wherein X represents Ile (found at that position in gp130 and LIF-R) or Val (for IL-2Rγ). Additional 5' primers degenerate to the sequence LeuGlnIleArgCys (SEQ ID NO:10), which is found at the corresponding position in G-CSF-R, were employed as well. The 3' primers were degenerate to the amino acid sequence TrpSerXTrpSer (SEQ ID NO:11), which is found at positions 288–292 of the gp130 sequence of SEQ ID NO:2, wherein X represents Asp (found at that position in gp130 and LIF-R), Lys (for LIF-R), or Glu (for IL-2Rγ).

To test the viability of this approach, PCR was conducted using the above-described primers with LIF-R, gp 130, G-CSF-R, or IL-2Rγ DNA as the template. The reactions were conducted by conventional techniques, and the reaction products were analyzed by gel electrophoresis. For each reaction, a band about 50 base-pairs in size was seen on the gel, indicating successful amplification of a DNA fragment of the expected size.

PCR was then conducted using genomic human DNA as the template. The reaction products were analyzed by gel electrophoresis, and a 50 bp band was visualized. This band was excised from the gel, and the DNA was eluted therefrom. The DNA was subcloned into the cloning vector pBLUESCRIPT® SK, which is available from Stratagene Cloning Systems, La Jolla, Calif. *E. coli* cells were transformed with the resulting recombinant vectors, and individual colonies of the transformants were cultivated in 96-well plates.

Twelve colonies were chosen at random, and the recombinant vectors were isolated therefrom. The nucleotide sequences of the DNA inserts of the vectors were determined. Seven of these inserts were identified by their sequence as gp130 DNA, two were LIF-R, one contained a stop codon and did not appear to be of interest, and two contained a novel sequence (the same sequence, in both orientations). An oligonucleotide probe containing this novel sequence (the portion of the insert that is between the two primer sequences) was prepared and labeled with $^{32}$P by standard techniques.

The $^{32}$P-labeled probe was used to screen two different cDNA libraries, one derived from human placenta and the other from a cell line designated IMTLH-1. The placental library was chosen because placenta is a rich source of growth and differentiation factors. The IMTLH cells, obtained by transformation of human bone marrow stromal cells with pSV-neo, were chosen because they were found to bind oncostatin M but not LIF (Thoma et al., *J. Biol. Chem.* 269:6215, 1994). In addition, an RNA band of about 5.5–6.0 kb was detected on Northern blots of RNA derived from IMTLH-1 cells and placenta, probed with the above-identified $^{32}$P-labeled probe.

Positive clones were isolated from both libraries and determined by DNA sequencing to contain various portions of the novel DNA of interest. Although an initiator codon (indicating the 5' end of a coding region) was identified, none of the clones appeared to contain the stop codon that would represent the 3' end of the coding region.

An oligonucleotide probe corresponding to sequence found near the 3' end of several of the clones was synthesized and labeled with $^{32}$P by standard techniques. The probe was used to screen a cDNA library derived from the SV40-transformed human lung fibroblast cell line WI-26 VA4. This library was constructed as described in example 2 of U.S. Pat. No. 5,264,416, which is hereby incorporated by reference. Clones comprising additional coding sequence at the 3' end (compared to the previously-identified clones above) were isolated.

An expression vector was constructed, containing a DNA fragment comprising this 3' end of the novel sequence ligated to DNA fragments from the above-described clones containing the 5' end of the novel sequence. The nucleotide sequence of the human OSM-Rβ DNA in the resulting recombinant vector is presented in SEQ ID NO:5. The protein encoded by the isolated DNA is presented in SEQ ID NO:6.

The vector was a mammalian expression vector designated pDC409. This vector is similar to pDC406, described in McMahan et al., (*EMBO J.* 10:2821, 1991). A Bgl II site outside the multiple cloning site (mcs) in pDC406 has been deleted so that the BglII site in the mcs of pDC409 is unique. The pDC409 multiple cloning site (mcs) differs from that of pDC406 in that it contains additional restriction sites and three stop codons (one in each reading frame). A T7 polymerase promoter downstream of the mcs facilitates sequencing of DNA inserted into the mcs.

The OSM-Rβ cDNA insert was excised from an expression vector using restriction enzymes that cleave within the 5' and 3' non-coding regions of the cDNA. The excised cDNA was ligated into the EcoRV site of the cloning vector pBluescript® SK[31] (Stratagene Cloning Systems, LaJolla, Calif.). The Eco RV site, found in the multiple cloning site of the vector, was destroyed by insertion of the cDNA. *E. coli* cells transformed with the resulting recombinant vector were deposited with the American Type Culture Collection, Rockville, Md., U.S.A., on Aug. 16, 1994, and assigned accession no. ATCC 69675. The deposit was made under the terms of the Budapest Treaty.

The encoded OSM-Rβ amino acid sequence presented in SEQ ID NO:6 comprises an N-terminal signal peptide (amino acids −27 to −1) followed by an extracellular domain (amino acids 1 to 714), a transmembrane region (amino acids 715 to 734) and a cytoplasmic domain (amino acids 735 to 952). The OSM-Rβ amino acid sequence is approximately 30% identical to that of the LIF receptor protein described in Gearing et al. (*EMBO J.* 10:2839, 1991) and in U.S. Pat. No. 5,284,755, hereby incorporated by reference. The DNA sequence of the coding region of OSM-Rβ is about 48% identical to the portion of LIF-R DNA that aligns with the OSM-Rβ coding region when the above-described GAP computer program is employed.

Example 2

Assay to Detect Binding of Oncostatin M

An assay for binding of oncostatin M by cells expressing both recombinant gp130 and recombinant OSM-Rβ was conducted as follows. An assay for oncostatin M binding by cells expressing gp130 alone was also conducted for purposes of comparison.

Oncostatin M may be purified from cells in which the protein is naturally found, or from cells transformed with an expression vector encoding oncostatin M. One source of oncostatin M is phorbol ester-treated U937 cells, as described by Zarling et al., *PNAS U.S.A.* 83:9739 (1986). Purification of recombinant oncostatin M is described by Linsley et al. (*J. Biol. Chem.* 264:4282–4289, 1989) and Gearing et al. (*EMBO J.* 10:2839, 1991).

Oncostatin M (OSM) may be radiolabeled using any suitable conventional procedure. Radioiodination of oncostatin M has been described by Linsley et al., supra., for example. In one suitable procedure, OSM is radiolabeled using a commercially available enzymobead radioiodination reagent (BioRad) according to manufacturer's instructions. The resulting $^{125}$I-OSM is diluted to a working stock solution in binding medium, which is RPMI 1640 medium containing 2.5% (w/v) bovine serum albumin (BSA), 0.2% (w/v) sodium azide, and 20 mM Hepes, pH 7.4.

CV1-EBNA-1 cells in 150 mm dishes ($3.6 \times 10^6$ cells/dish) were transfected with a gp130-encoding expression vector, or were co-transfected with the gp130-encoding vector and an OSM-Rβ-encoding vector. All cells were additionally co-transfected with a mammalian expression vector designated pDC410, described below.

The OSM-Rβ-encoding vector was the recombinant vector described in example 1, comprising full length OSM-Rβ DNA in mammalian expression vector pDC409. The gp130-encoding vector comprised the human gp130 DNA sequence of SEQ ID NO:1 in a mammalian expression vector designated pDC304. A similar recombinant vector, comprising the same gp130-encoding DNA in mammalian expression vector pDC303, was deposited in *E. coli* strain DH5α host cells with the American Type Culture Collection, Rockville, Md. These transformed cells were deposited under the name B10G/pDC303 (DH5α) on Nov. 14, 1991 and assigned ATCC Accession No. 68827. The deposit was made under the terms of the Budapest Treaty.

pDC304 comprises a NotI site in its multiple cloning site, but is otherwise identical to pDC303. pDC304 also is essentially identical to pCAV/NOT, described in PCT application WO 90/05183, except that a segment of the adenovirus-2 tripartite leader (TPL) containing a cryptic promoter functional in bacteria has been deleted. Protein expression from the cryptic promoter is potentially disadvantageous for preparing and isolating a desired recombinant plasmid in bacterial cells.

The pDC410 vector is identical to the pDC409 vector described in example 1, except that the EBV origin of replication of pDC409 is replaced by DNA encoding the SV40 large T antigen driven from the SV40 promoter in pDC410. Co-transfecting the cells with this vector provides the SV40 T-antigen that drives high level DNA replication of the other plasmid vectors, which contain the SV40 origin of replication. pDC410 thus is important for episomal replication of the co-transfected vectors in CV1-EBNA-1 cells.

The transfected cells were cultured for 24 hours, trypsinized and replated, then cultured another 24 hours to permit expression of the encoded proteins, which were retained on the cell membrane. The adherent cells were dislodged using 5 mM EDTA in PBS, then washed twice with binding medium (RPMI 1640 medium containing 25 mg/ml bovine serum albumin, 2 mg/ml sodium azide, and 20 mM HEPES, pH 7.2). The cells then were incubated with various concentrations of $^{125}$I-labeled oncostatin M in binding medium for 1 hour at 37° C. with gentle agitation.

Free and cell-bound $^{125}$I-oncostatin M were separated using the phthalate oil separation method of Dower et al. (*J. Immunol.* 132:751, 1984), essentially as described by Park et al. (*J. Biol. Chem.* 261:4177, 1986, and *Proc. Natl. Acad. Sci. USA* 84:5267, 1987). The free and cell-bound $^{125}$I-oncostatin M were quantified on a Packard Autogamma Counter. Affinity calculations (Scatchard, *Ann. N.Y. Acad. Sci.* 51:660, 1949) were generated on RS/1 (BBN Software, Boston, Mass.) run on a Microvax computer.

Figure 2:
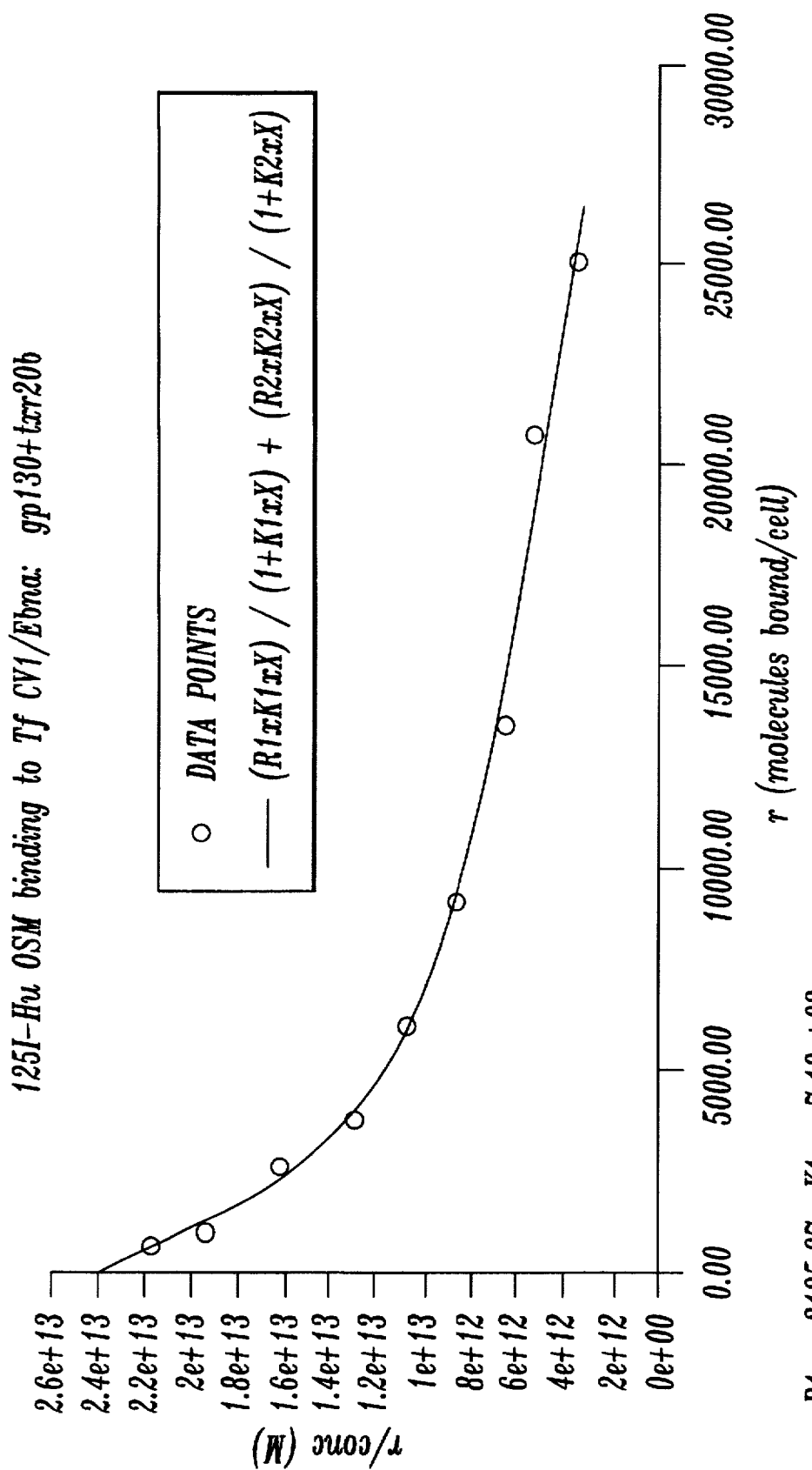
FIG. 2 presents a Scatchard analysis of the results of an assay for binding of radioiodinated oncostatin M by cells expressing both recombinant gp130 and recombinant OSM-Rβ. As described in example 2, the data in FIG. 2 demonstrate higher affinity oncostatin M binding compared to the oncostatin M binding by gp130 alone depicted in FIG. 1.

The results are presented in FIGS. 1 and 2, in the form of Scatchard analyses. FIG. 1 presents the results for cells expressing gp130 alone. These transfected cells exhibited a single affinity class of binding, with approximately 29,310 receptor sites per cell, and an affinity constant (Ka) of $2.64 \times 10^8$. FIG. 2 presents the results for cells expressing gp130 and OSM-Rβ. A biphasic pattern can be seen, indicating two binding components. The first component (approximately 2196 receptor sites per cell) exhibited an affinity constant of $7.18 \times 10^9$. The second component (approximately 36,471 receptor sites per cell) exhibited an affinity constant of $2.34 \times 10^8$. Thus, a relatively high affinity binding component is seen in the cells expressing both gp130 and OSM-Rβ. These high affinity binding sites were absent in the cells expressing gp130 alone.

The cells co-transfected with both OSM-Rβ- and gp130-encoding expression vectors expressed a receptor protein of the present invention. The receptor binds oncostatin M with higher affinity than does the gp130 protein expressed on cells transfected with the gp130-encoding vector alone.

Example 3

Preparation of Monoclonal Antibodies Directed Against OSM-Rβ

Purified OSM-Rβ polypeptides of the present invention are employed as immunogens to generate monoclonal antibodies immunoreactive therewith using conventional techniques, for example, those disclosed in U.S. Pat. No. 4,411,993. Suitable immunogens include, but are not limited to, full length recombinant OSM-Rβ or fragments thereof, such as the extracellular domain. To immunize mice, the immunogen is emulsified in complete Freund's adjuvant and injected subcutaneously in amounts ranging from 10–100 μg into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable.

Following detection of an appropriate antibody titer, positive animals are given an intravenous injection of antigen in saline. Three to four days later, the animals are sacrificed, splenocytes harvested, and fused to a murine myeloma cell line, e.g., NS1 or, preferably, P3×63Ag8.653 (ATCC CRL 1580). Hybridoma cell lines generated by this procedure are plated in multiple microtiter plates in a HAT selective medium (hypoxantine, aminopterin, and thymidine) to inhibit proliferation of non-fused cells, myeloma hybrids, and spleen cell hybrids.

Hybridoma clones thus generated can be screened by ELISA for reactivity with the receptor protein, for example, by adaptations of the techniques disclosed by Engvall et al., *Immunochem* 8,871 (1971) and in U.S. Pat. No. 4,704,004. A preferred screening technique is the antibody capture technique described in Beckmann et al. (*J. Immunol.* 144:4212, 1990). Positive clones are then injected into the peritoneal cavities of syngeneic Balb/c mice to produce ascites containing high concentrations (greater than 1 mg/ml) of anti-OSM-Rβ monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 4

Receptors Comprising gp130 Polypeptides Lacking FNIII Domains

DNA sequences encoding soluble gp130 proteins lacking fibronectin type III (FNIII) domains were isolated and fused to an Fc-encoding sequence. Deleting the FNIII domains affords the advantage of reducing the size of the gp130/Fc fusion protein. gp130 contains three FNIII domains, comprising amino acids 300 (Tyr) to 399 (Phe), 400 (Gln) to 496 (Pro), and 497 (Pro) to 597 (Glu), respectively, of SEQ ID NO:2. From one to all three of the FNIII domains may be removed from gp130 to reduce the size of the protein.

The FNIII domains of gp130 were removed by digesting a recombinant gp130/Fc-encoding expression vector with BstX1, then blunting the overhang using T4 DNA polymerase according to conventional procedures. The recognition site for BstX1 spans nucleotides 1231–1242 of SEQ ID NO:1 (gp130), cleaving within the codons for amino acids 10–11 of the first FNIII domain of gp130. The cleaved vector was then digested with EcoR5, which cleaves within the polylinker of the vector upstream of the Fc sequence and generates blunt ends. The (BstX1)/EcoR5 fragment comprising a sequence encoding the 5' end of gp130 (lacking the FNIII domains), the vector sequences, the Fc sequence, and a portion of the polylinker, was ligated to recircularize the vector.

*E. coli* cells were transformed with the ligation mixture, plasmids were isolated therefrom, and the desired recombinant plasmid was identified by restriction analysis. The fusion protein encoded by the construct comprises (from N- to C-terminus) amino acids –22 to 308 of SEQ ID NO:2 (gp130), a four amino acid spacer peptide-Asn-Arg-Tyr-Val-encoded by the polylinker segment, and amino acids 1–232 of SEQ ID NO:3 (Fc). The gp130 polypeptide moiety contains the first 9 amino acids of the first FNIII domain, but lacks the remainder of the first FNIII domain and all of the second and third FNIII domains.

A heterodimeric receptor of the present invention may comprise OSM-Rβ and the foregoing truncated gp130 polypeptide lacking FNIII domains. COS-7 cells or other suitable host cells are co-transfected with OSM-Rβ-encoding and truncated gp130-encoding expression vectors. The co-transfected cells are cultured to express the heterodimeric receptor.

Example 5

Assay for Binding of Oncostatin M and LIF by Receptors

An assay for binding of oncostatin M or leukemia inhibitory factor (LIF) by various receptor proteins was conducted as follows. The receptor proteins included soluble OSM-Rβ/Fc, gp130/Fc, LIF-R/Fc, and combinations thereof. Results of the assay are presented in FIG. 3.

An expression vector encoding a soluble OSM-Rβ/Fc fusion protein, which comprised a truncated extracellular domain of OSM-Rβ fused to the N-terminus of an Fc region polypeptide derived from an antibody, was constructed as follows. The recombinant expression vector prepared in example 1, comprising OSM-Rβ DNA in vector pDC409, was digested with the restriction enzyme SphI, treated with T4 DNA polymerase to remove the 3' overhangs (generating blunt ends), then digested with Sal I, which cleaves upstream of the OSM-Rβ coding region. The desired fragment, which includes the 5' end of the OSM-Rβ DNA, terminating at nucleotide 1744 of SEQ ID NO:5, was isolated by conventional techniques.

A recombinant vector designated hIgG1Fc comprises the Fc polypeptide-encoding cDNA of SEQ ID NO:3, as described above. Vector hIgG1Fc was digested with the restriction enzymes Sna B1 and NotI, which cleave in the polylinker region of the vector, upstream and downstream, respectively, of the Fc polypeptide-encoding cDNA.

The thus-isolated Fc polypeptide-encoding DNA fragment and the OSM-Rβ-encoding DNA fragment isolated above were ligated into a SalI/NotI-digested expression vector pDC304 such that the Fc polypeptide DNA was fused to the 3' end of the OSM-Rβ DNA. The mammalian expression vector pDC304 is described in example 2. The resulting expression vector encoded a fusion protein comprising amino acids −27 through 432 of the OSM-Rβ sequence of SEQ ID NO:6, followed by a valine residue encoded by a vector polylinker segment, followed by amino acids 1 through 232 of the Fc polypeptide sequence of SEQ ID NO:4.

An expression vector encoding a soluble human gp130/Fc fusion protein was constructed as follows. Recombinant vector B10G/pDC303 (ATCC 68827) comprising human gp130 cDNA was digested with EcoR1, and the resulting 5' overhang was rendered blunt using T4 DNA polymerase. The recognition site for EcoR1 comprises nucleotides 2056–2061 of SEQ ID NO:1. The EcoR1-digested vector was then cleaved with XhoI, which cleaves in the vector upstream of the gp130 cDNA insert.

Vector hIgG1Fc, comprising Fc polypeptide-encoding cDNA as described above, was digested with StuI (a blunt cutter) and NotI, which cleave upstream and downstream, respectively, of the inserted Fc cDNA. The XhoI/(EcoR1) gp130 fragment isolated above was ligated to the Fc-containing fragment and to XhoI/NotI-digested mammalian expression vector pDC304.

E. coli cells were transformed with the ligation mixture, plasmids were isolated therefrom by conventional procedures, and the desired recombinant vector was identified by restriction analysis. The gp130/Fc fusion protein encoded by the recombinant vector comprises (from N- to C-terminus) amino acids −22 to 582 of SEQ ID NO:2 (gp130), followed by 7 amino acids constituting a peptide linker encoded by the polylinker segment of plasmid hIgG1Fc, followed by amino acids 1–232 of SEQ ID NO:4 (Fc).

An expression vector encoding a soluble human LIF-R/Fc fusion protein was constructed as described in example 5 of U.S. Pat. No. 5,284,755, hereby incorporated by reference. Briefly, a recombinant vector designated pHLIF-R-65 contains human LIF-R cDNA (a partial clone encoding a complete signal peptide, extracellular domain, and transmembrane region, and a partial cytoplasmic domain) in vector pDC303. The mammalian expression vector pDC303 is described in PCT application WO 93/19777. E. coli cells transformed with pHLIF-R-65 were deposited with the American Type Culture Collection, Rockville, Md., on Dec. 11, 1990, and assigned accession no. 68491. DNA encoding the LIF-R signal peptide and extracellular domain (truncated at the C-terminus) was isolated and fused to DNA encoding an antibody Fc region polypeptide in pBluescript®SK⁻. The gene fusion was excised from the cloning vector and inserted into the above-described mammalian expression vector pDC304. The resulting recombinant expression vector encoded a LEF-R/Fc fusion protein comprising amino acids −44 through 702 of the LIF-R sequence presented in U.S. Pat. No. 5,284,755, followed by a linker comprising six amino acids encoded by a vector polylinker segment, followed by amino acids 1 through 232 of the Fc amino acid sequence of SEQ ID NO:4.

CV-1-EBNA cells were transfected with one of the three recombinant expression vectors prepared above, or co-transfected with two of the vectors, as follows:

| Experiment | Cells transfected with vector(s) encoding: |
|---|---|
| A | empty expression vector (control) |
| B | gp130/Fc |
| C | LIF-R/Fc |
| D | OSM-Rβ/Fc |
| E | OSM-Rβ/Fc and LIF-R/Fc |
| F | OSM-Rβ/Fc and gp130/Fc |
| G | gp130/Fc and LIF-R/Fc |

The transfected cells were cultured to allow expression and secretion of the fusion proteins into the culture medium. Cross-linked agarose beads bearing Protein A (Protein A Sepharose CL-4B, Pharmacia Biotech, Inc., Piscataway, N.J.) were added to the culture supernatants, whereupon the fusion proteins bound to the beads via the interaction of the Fc moiety with the Protein A. Radioiodinated oncostatin M or radioiodinated LIF was also added to the culture supernatants. Preparation of $^{125}$I-oncostatin M is described in example 2 above. Among the known procedures for purifying and radioiodinating LIF are those described in example 1 of U.S. Pat. No. 5,284,755. The $^{125}$I-LIF employed in this assay was recombinant human LIF labeled with $^{125}$I using the enzymobead reagent (BioRad).

The culture supernatants were incubated with the Protein A beads and $^{125}$I-LIF or $^{125}$I-oncostatin M for 18 hours at 4° C. Free and cell-bound $^{125}$I-LIF or $^{125}$I-oncostatin M were separated by low speed centrifugation through a single step density gradient of 3% glucose in PBS. The bead-bound radioiodinated proteins were quantified on a Packard Autogamma counter.

Figure 3:
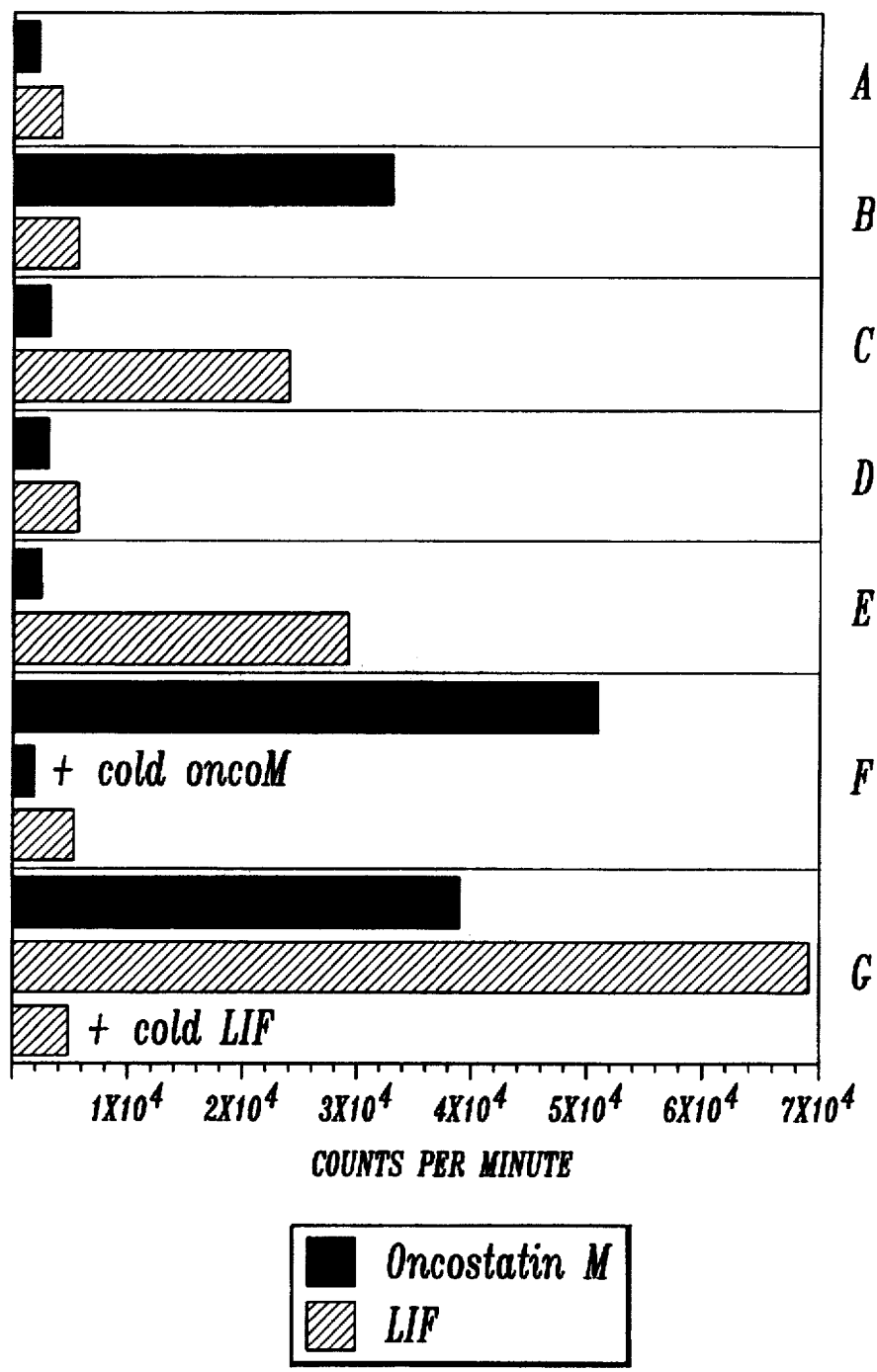
FIG. 3 is a bar graph representing binding of leukemia inhibitory factor (LIF) and oncostatin M to various receptor proteins, as described in example 5.

The results are presented in FIG. 3. The bar graph in FIG. 3 represents the binding of oncostatin M or LIF to the proteins expressed by cells transfected as described above for experiments A to G. The expressed proteins are bound to the Protein A beads.

Experiment A (control) revealed no significant binding of LIF or oncostatin M to proteins expressed by cells transfected with the empty expression vector pDC304. The soluble gp130/Fc protein bound oncostatin M, but no significant binding of LIF was demonstrated (experiment B). The soluble LIF-RIFc protein bound LIF, but not oncostatin M (experiment C). No detectable binding of LIF or oncostatin M by the soluble OSM-Rβ/Fc protein was demonstrated (experiment D).

Proteins expressed by cells co-transfected with soluble LIF-R/Fc and OSM-Rβ encoding vectors did not bind detectable quantities of oncostatin M, but bound LIF (experiment E). Proteins expressed by cells co-transfected with soluble OSM-Rβ/Fc and soluble gp130/Fc encoding vectors bound oncostatin M, but did not bind detectable quantities of LIF (experiment F). The binding of oncostatin M in experiment F could be inhibited by including unlabeled (cold) oncostatin M in the assay. The proteins expressed by cells co-transfected with expression vectors encoding soluble gp130/Fc and LIF-R/Fc (experiment G) bound both oncostatin M and LIF. The LIF binding in experiment G was inhibited by adding cold LIF to the assay.

The proteins expressed when cells are co-transfected with vectors encoding soluble OSM-Rβ/Fc and soluble gp130/Fc, in accordance with the present invention, thus bind oncostatin M but not LIF. This is advantageous when binding of oncostatin M (e.g., to inhibit or study a biological activity thereof) is desired, but binding of LIF is not desired. The proteins expressed by cells co-transfected with soluble gp130/Fc and soluble LIF-R/Fc encoding vectors bind both oncostatin M and LIF, and thus do not offer this advantageous property. In addition, cells expressing both soluble OSM-Rβ/Fc and soluble gp130/Fc bound oncostatin M at a higher level than did cells expressing soluble gp130/Fc alone.

BRIEF DESCRIPTION OF THE SEQUENCE LISTING

SEQ ID NO:1 and SEQ ID NO:2 present the DNA sequence and encoded amino acid sequence for cloned cDNA encoding an N-terminal fragment of gp130.

SEQ ID NO:3 and SEQ ID NO:4 present the DNA sequence and encoded amino acid sequence for cloned cDNA encoding a polypeptide that corresponds to the Fc region of an IgG1 antibody.

SEQ ID NO:5 and SEQ ID NO:6 present the DNA and encoded amino acid sequence for cloned cDNA encoding the oncostatin M receptor β subunit of the present invention.

SEQ ID NO:7 presents the amino acid sequence of a peptide that may be employed to facilitate purification of polypeptides fused thereto.

SEQ ID NO:8 presents a spacer peptide encoded by a polylinker in an expression vector, as described in example 4.

SEQ ID NOS:9, 10, and 11 are peptides that correspond to conserved sequences, as described in example 1.

---

What is claimed is:

1. A purified receptor capable of binding oncostatin M, comprising a gp130 polypeptide covalently linked to an oncostatin M receptor β-chain (OSM-Rβ) polypeptide, wherein:
   a) said gp130 polypeptide is selected from the group consisting of:
      i) a gp130 polypeptide comprising amino acids 1 to 686 of SEQ ID NO:2; and
      ii) a fragment of the polypeptide of (i);
   b) said OSM-Rβ polypeptide is selected from the group consisting of:
      iii) an OSM-Rβ polypeptide comprising amino acids 1 to 952 of SEQ ID NO:6; and
      iv) a fragment of the polypeptide of iii;
   wherein said receptor comprising a gp130 polypeptide and an OSM-Rβ polypeptide binds oncostatin M with higher affinity than does the gp130 polypeptide alone.

2. A receptor according to claim 1, wherein said receptor comprises a soluble gp130 polypeptide covalently linked to a soluble OSM-Rβ polypeptide.

3. A receptor according to claim 1 wherein said receptor comprises gp130 covalently linked to OSM-Rβ via a peptide linker.

4. A receptor according to claim 3, wherein said receptor is a recombinant fusion protein of the formula:

$R_1$-L-$R_2$ or $R_2$-L-$R_1$ wherein $R_1$ represents a soluble gp130; $R_2$ represents a soluble OSM-Rβ, and L represents a peptide linker.

5. A receptor capable of binding oncostatin M, comprising a soluble gp130 polypeptide covalently linked to a soluble oncostatin M receptor β-chain (OSM-Rβ) polypeptide, wherein said soluble gp130 comprises amino acids −22 to y or 1 to y of SEQ ID NO:2, wherein y represents an integer between 308 and 597, inclusive; and said soluble OSM-Rβ comprises amino acids −27 to x or 1 to x of SEQ ID NO:6, wherein x is an integer between 432 and 714, inclusive.

6. A purified receptor comprising a first fusion polypeptide that comprises an antibody Fc region polypeptide attached to the C-terminus of a soluble gp130, and a second fusion polypeptide that comprises an antibody Fc region polypeptide attached to the C-terminus of a soluble OSM-Rβ, wherein said first fusion polypeptide is linked to said second fusion polypeptide via disulfide bonds between the Fc region polypeptides;
   wherein said soluble gp130 comprises amino acids 1 to y of SEQ ID NO:2, wherein y represents an integer between 308 and 597, inclusive; and said soluble OSM-Rβ comprises amino acids 1 to x of SEQ ID NO:6, wherein x is an integer between 432 and 714, inclusive.

7. A composition comprising a receptor of claim 2 and a suitable diluent or carrier.

8. A purified receptor capable of binding oncostatin M, comprising a gp130 polypeptide covalently linked to an oncostatin M receptor β-chain (OSM-Rβ) polypeptide, wherein;
   said gp130 polypeptide is encoded by a DNA selected from the group consisting of:

a) DNA comprising the coding region of the nucleotide sequence presented in SEQ ID NO:1;
b) a naturally occurring DNA capable of hybridizing to the DNA of (a) under highly stringent conditions that include hybridization at 68° C. followed by washing in 0.1× SSC/0.1% SDS at 63°–68° C.; and
c) DNA that encodes the amino acid sequence presented in SEQ ID NO:2;

said OSM-Rβ polypeptide is encoded by a DNA selected from the group consisting of:

a') DNA comprising the coding region of the nucleotide sequence presented in SEQ ID NO:5;
b') a naturally occurring DNA capable of hybridizing to the DNA of (a') under highly stringent conditions that include hybridization at 68° C. followed by washing in 0.1× SSC/0.1% SDS at 63°–68° C.; and
c') DNA that encodes the amino acid sequence presented in SEQ ID NO:6;

wherein said receptor comprising a gp130 polypeptide and an OSM-Rβ polypeptide binds onconstatin M with higher affinity than does the gp130 polypeptide alone.

9. A receptor according to claim 5, wherein said soluble gp130 comprises amino acids 1 to y of SEQ ID NO:2, wherein y represents an integer between 308 and 597, inclusive; and said soluble OSM-Rβ comprises amino acids 1 to x of SEQ ID NO:6, wherein x is an integer between 432 and 714, inclusive.

10. A composition comprising a receptor of claim 1, and a suitable diluent or carrier.

11. A composition comprising a receptor of claim 5, and a suitable diluent or carrier.

12. A composition comprising a receptor of claim 6, and a suitable diluent or carrier.

13. A purified receptor capable of binding oncostatin M, comprising a gp130 polypeptide covalently linked to an oncostatin M receptor β-chain (OSM-Rβ) polypeptide, wherein:

said gp130 polypeptide comprises modification(s) in the sequence of amino acids 1 to y of SEQ ID NO:2, wherein y represents an integer between 308 and 597, inclusive;

said OSM-Rβ polypeptide comprises modification(s) in the sequence of amino acids 1 to x of SEQ ID NO:6, wherein x is an integer between 432 and 714, inclusive;

wherein said modification(s) are selected from the group consisting of:
a) inactivation of N-glycosylation site(s);
b) inactivation of KEX2 protease processing site(s);
c) deletion of cysteine residue(s); and
d) substitution of cysteine residue(s) with non-cysteine residue(s).

* * * * *